US008642083B2

(12) United States Patent
Kim et al.

(10) Patent No.: US 8,642,083 B2
(45) Date of Patent: Feb. 4, 2014

(54) CONTROLLED RELEASE COMPLEX COMPOSITION COMPRISING ANGIOTENSIN-II-RECEPTOR BLOCKERS AND HMG-COA REDUCTASE INHIBITORS

(75) Inventors: Sung Wuk Kim, Seongnam-si (KR); Sung Soo Jun, Seongnam-si (KR); Young Gwan Jo, Daejeon (KR); Ja Seong Koo, Daejeon (KR); Jae Woon Son, Suwon-si (KR)

(73) Assignee: Hanall Biopharma Co., Ltd., Daejeon (KR)

( * ) Notice: Subject to any disclaimer, the term of this patent is extended or adjusted under 35 U.S.C. 154(b) by 63 days.

(21) Appl. No.: 12/513,054

(22) PCT Filed: Oct. 30, 2007

(86) PCT No.: PCT/KR2007/005405
§ 371 (c)(1),
(2), (4) Date: Jul. 10, 2009

(87) PCT Pub. No.: WO2008/054123
PCT Pub. Date: May 8, 2008

(65) Prior Publication Data
US 2010/0074951 A1    Mar. 25, 2010

(30) Foreign Application Priority Data
Oct. 30, 2006  (KR) .................. 10-2006-0105617

(51) Int. Cl.
A61K 9/42    (2006.01)
A61K 9/40    (2006.01)
A61K 9/36    (2006.01)
A61K 9/28    (2006.01)
A61K 9/20    (2006.01)

(52) U.S. Cl.
USPC ........... 424/476; 424/464; 424/474; 424/478; 424/480

(58) Field of Classification Search
USPC .................... 424/476, 464, 474, 478, 480
See application file for complete search history.

(56) References Cited

U.S. PATENT DOCUMENTS

| 5,138,069 A | 8/1992 | Carini et al. | |
| 6,228,398 B1 * | 5/2001 | Devane et al. | 424/484 |
| 2007/0254932 A1 * | 11/2007 | Tomiyama et al. | 514/381 |
| 2008/0096866 A1 | 4/2008 | Woo et al. | |

FOREIGN PATENT DOCUMENTS

| ER | 1275373 A1 | 1/2003 |
| JP | 2001-78686 A | 3/2001 |
| JP | 2001/078681 A1 | 10/2001 |
| KR | 10-0582347 B1 | 5/2006 |
| WO | 9933448 A1 | 7/1999 |
| WO | 0115674 A1 | 3/2001 |
| WO | 03020243 A1 | 3/2003 |
| WO | 2005/009413 A1 | 2/2005 |
| WO | 2005009413 A1 | 2/2005 |
| WO | 2006/071077 A1 | 7/2006 |
| WO | WO 2008/010008 * | 1/2008 ........... A61K 31/549 |

OTHER PUBLICATIONS

Sheng-Fang Su, et al, Effects of Pravastatin on Left Ventricular Mass in Patients With Hyperlipidemia and Essential Hypertension, 86 Am. J Cardiol. 514 (2000).*
Georg Nickening, Should Angiotensin-II-Receptor Blockers and Statins be Combined?, 110 Circulation 1013, 1014-17 (Aug. 24, 2004).*
Alberto Corsini, The Safety of HHMG-CoA Reductase Inhibitors in Special Populations at High Cardiovascular Risk, 17 Cardio. Drugs Therapy 265, 266-67, 271-72 (2003).*
Maria Marino, et al, Irbesartan Does Not Affect the Pharmacokinetics of Simvastatin in Healthy Subjects, 40 J Clin. Pharmacol. 875 (2000).*
P. Wilson, et al.: "Coronary Risk Prediction in Adults (The Framingham Heart Study)," Am. J. Cardiol. vol. 59, pp. 91G-94G, 1987.
J. Wagner, et al.: "Effects of AT1 Receptor Blockade on Blood Pressure and the Renin-Angiotensin System in Spontaneously Hypertensive Rats of the Stroke Prone Strain," Clin. Exper. Hypertens., vol. 20, No. 2, pp. 205-221, 1998.
M. Böhm, et al.: "Angiotensin II receptor blockade in TGR(mREN2)27: effects of renin-angiotensin-system gene expression and cardiovascular functions," J. Hypertens., vol. 13, No. 8, pp. 891-899, 1995.
S. Andersen, et al.: "Renoprotective effects of angiotensin II receptor blockade in type 1 diabetic patients with diabetic nephropathy," Kid. Internat., vol. 57, pp. 601-606, 2000.
L. Ruilope: "Renoprotection and Renin-Angiotensin System Blockade in Diabetes Mellitus," Am. J. Hypertens., vol. 10, No. 12, pp. 325S-331S, Dec. 1997.
E. Schiffrin, et al.: "Correction of Arterial Structure and Endothelial Dysfunction in Human Essential Hypertension by the Angiotensin Receptor Antagonist Losartan," Circulation, vol. 101, pp. 1653-1659, Apr. 11, 2000.
R. Touyz, et al.: "Angiotensin II stimulates DNA and protein synthesis in vascular smooth muscle cells from human arteries: role of extracellular signal-regulated kinases," J. Hypertens., vol. 17, No. 7, pp. 907-916, 1999.

(Continued)

Primary Examiner — Sean Basquill
(74) Attorney, Agent, or Firm — Rothwell, Figg, Ernst & Manbeck, P.C.

(57) ABSTRACT

Disclosed herein is a lag time delayed-release combination pharmaceutical composition comprising of an angiotensin-II-receptor blocker and an HMG-CoA reductase inhibitor, as well as a preparation method thereof. The composition is designed based on chronotherapy in which active ingredients are administered to have different onset times, such that the release of each active ingredient of the composition in body can be lag time delayed to a specific rate. Also, the composition is very effective for the treatment of hypertension and the prevention of complications in patients having metabolic syndromes which show diabetes, obesity, hyperlipidemia, coronary artery diseases and the like. More specifically, the composition is a drug delivery system designed such that the release of each drug is controlled to a specific rate, and it can show the most ideal effect, when it is absorbed in body.

42 Claims, 10 Drawing Sheets

(56) References Cited

OTHER PUBLICATIONS

A. Prasad, et al.: "Acute and Chronic Angiotensin-1 Receptor Antagonism Reverses Endothelial Dysfunction in Atherosclerosis," Circulation, vol. 101, pp. 2349-2354, May 23, 2000.

E. Schiffrin: "Vascular Remodeling and Endothelial Function in Hypertensive Patients: Effects of Antihypertensive Therapy," Scand. Cardiovasc. J. Suppl., vol. 32, supp. 47, pp. 15-21, 1998.

T. Pedersen et al.: "Randomised trial of cholesterol lowering in 4444 patients with coronary heart disease" The Lancet, vol. 344, pp. 1383-1389, Nov. 19, 1994.

K. Gould, et al.: "Non-invasive management of coronary artery disease," The Lancet, vol. 346, pp. 750-753, Sep. 16, 1995.

J. Shepherd: "Preventing Coronary Artery Disease in the West of Scotland: Implications for Primary Prevention," Am. J. Cardiol., vol. 82, No. 10B, pp. 57T-59T, Nov. 26, 1998.

A. Tonkin, et al.: "Management of the Long-term Intervention with Pravastatin in Ischaemic Disease (LIPID) Study after the scandinavian Simvastatin Survival Study (4S)," Am. J. Cardiol., vol. 76, pp. 107C-112C, Sep. 28, 1995.

K. Matsubara, et al.: "Current Status of Lipid Management of Hypertensive Patients," Hypertens. Res., vol. 26, No. 9, pp. 699-704, 2003.

M. Minami, et al.: "Effects of Cholesterol-Lowering Therapy on Pressor Hyperreactivity to Stress in Hypercholesterolemic Patients," Hypertens. Res., vol. 26, No. 4, pp. 273-280, 2003.

D. Wood: "Asymptomatic individuals—risk stratification in the prevention of coronary heart disease," Br. Med. Bull., vol. 59, pp. 3-16, 2001.

A. Gotto: "Risk Factor Modification: Rationale for Management of Dyslipidemia," Am. J. Med., vol. 104, No. 2A, pp. 6S-8S, 1998.

D. Williams, et al.: "Pharmacokinetic-Pharmacodynamic Drug Interactions with HMG-CoA Reductase Inhibitors," Clin. Pharmacokinet., vol. 41, No. 5, pp. 343-370, 2002.

S. Vickers, et al.: "Metabolic Disposition Studies on Simvastatin, A Cholesterol-Lowering Prodrug," Drug Metab. Dispos., vol. 18, No. 2, pp. 138-145, 1990.

S. Vickers, et al.: "In Vitro and in Vivo Biotransformation of Simvastatin, an Inhibitor of HMG CoA Reductase," Drug Metab. Dispos., vol. 18, No. 4, pp. 476-483, 1990.

T. Prueksaritanont, et al.: "In Vitro Metabolism of Simvastatin in Humans [SBT]Identification of Metabolizing Enzymes and Effect of the Drug on Hepatic P450S," Drug Metab. & Dispos., vol. 25, No. 10, pp. 1191-1199, 1997.

P. Neuvonen, et al.: "Simvastatin but not pravastatin is very susceptible to interaction with the CYP3A4 inhibitor itraconazole," Clin. Pharm. & Ther., vol. 63, No. 3, pp. 332-341, 1998.

T. Kantola, et al.: "Erythromycin and verapamil considerably increase serum simvastatin and simvastatin acid concentrations," Clin. Pharm. Ther., vol. 64, No. 2, pp. 177-182, 1998.

Physicians Desk Reference, "Zocor," 19 pages, 2006.

D. Sutton, et al.: "Role of CYP3A4 in Human Hepatic Diltiazem N-Demethylation: Inhibition of CYP3A4 Activity by Oxidized Diltiazem Metabolites," J. Pharmacol. Exp. Ther., vol. 282, No. 1, pp. 294-300, 1997.

D. Jones, et al.: "Diltiazem Inhibition of Cytochrom P-450 3A Activity Is Due to Metabolite Intermediate Complex Formation," J. Pharmacol. Exp. Ther., vol. 290, No. 3, pp. 1116-1125, 1999.

H. Watanabe, et al.: "Pharmacokinetic and pharmacodynamic interactions between simvastatin and diltiazem in patients with hypercholesterolemia and hypertension," Life Sci., vol. 76, pp. 281-292, 2004.

Y. Saito, et al.: "Comparison between morning and evening doses of simvastatin in hyperlipidemic subjects. A double-blind comparative study," Arterioscler. Thromb., vol. 11, No. 4, pp. 816-826, 1991.

D. Illingworth: "Comparative efficacy of once versus twice daily mevinolin in the therapy of familiar hypercholesterolemia," Clin. Pharmacol. Ther., vol. 40, No. 3, pp. 338-343, 1986.

Dept. of Medicine, Indiana University: "Cytochrome P450 Drug Interaction Table," http://medicine.iupui.edu/flockhart/ table.htm, 2 pages, updated Mar. 11, 2004.

Japanese Office Action issued in Japanese Application No. 2009-534505 on Jan. 11, 2012, with English translation, 6 pages.

Canadian Office Action issued in Canadian Application No. 2,564,893 on Jan. 13, 2012, 3 pages.

A. Hirata et al.: "Combination therapy with statin and other drugs in cardiovascular disease," The Circulation Frontier, vol, 7, No. 3, 2003, pp. 68-73.

K. Koh et al.: "Additive Benekial Effects of Losartan Combined With Simvastatin in the Treatment of Hypercholesterolemic, Hypertensive Patients," Circulation, vol. 110, No, 24, 2004, pp. 3687-3692.

J. Cockroft et al.: "Cholesterol reduction, statins and the cytochrome P-450 system." European Heart Journal, Vol, 21, No. 18, 2000, pp. 1555-1556.

Sekinco et al,: abstracts for Annual; Meeting at the Pharmaceutical Society of Japan, vol. 120, No. 4, 2000, p. 86.

* cited by examiner

CONTROLLED RELEASE COMPLEX COMPOSITION COMPRISING ANGIOTENSIN-II-RECEPTOR BLOCKERS AND HMG-COA REDUCTASE INHIBITORS

CROSS REFERENCE TO RELATED APPLICATIONS

This application is a 35 U.S.C. §371 National Phase Entry Application from PCT/KR2007/005405, filed Oct. 30, 2007, and designating the United States, which claims priority under 35 U.S.C. §119 to Korean Patent Application No. 10-2006-0105617 filed Oct. 30, 2006, which is incorporated herein in its entirety.

TECHNICAL FIELD

The present invention relates to a pharmaceutical combination composition comprising an angiotensin-II-receptor blocker and an HMG-CoA reductase inhibitor, which is designed based on xenobiotic-chronotherapy in which each component of combination composition is administered to have different onset time, such that each component of the combination composition may have a specific release rate, as well as a method for preparing the combination composition.

The delayed release combination composition according to the present invention is effective for the treatment of the hypertension with or without such complication as diabetes, other cardiovascular, renal disorders, metabolic syndromes like insulin resistance.

Specifically, the present invention relates to a drug delivery system, which is designed based on xenobiotic-chronotherapy in which each component of the combination product is dissolved with a specific release time in body and can show the most ideal effect, when it is absorbed in body.

The present invention is a functional lag time delayed release combination formulation technology developed for the first time in the world and is based on the following three platform technologies:
1) Xenobiotics: the application of the theory of the drug metabolism by the Enzymes;
2) Chronotherapy: the application of theory of the biorhythms in disease conditions; and
3) Drug delivery system (DDS): the application of the specific theory of the dissolution and absorption at different times.

BACKGROUND ART

Necessity of the Combination Product

Hypertension frequently coexists with coronary artery disease and both are considered to be major risk factors for developing cardiac disease. This clustering of risk factors is potentially due to a common mechanism. Arteriosclerosis, aggravated by hypertension and hyperlipidemia, is a condition which becomes worse when both symptoms are coexisting. When blood pressure increases, arteriosclerosis becomes worse, and when arteriosclerosis becomes worse, blood pressure increases to worsen arteriosclerosis. Also, these conditions are considered to be severe risk factors for developing cardiovascular diseases. For example, hypercholesterolemia and hyperlipidemia are involved in the early development of atherosclerosis, which is characterized in that lipid deposits are uniformly deposited inside artery including coronary artery, carotid artery and peripheral artery. Also, This irregular lipid deposition is thus characteristic of coronary heart damage and cardiovascular diseases, the gravity and prevalence of which are also affected by the existence of diabetes, the sex of the person, smoking, and left ventricular hypertrophy occurring as a side effect of hypertension [see Wilson et al., Am. J. Cardiol., vol. 59 (14) (1987), p. 91G-94G]. Thus, it is already well known that it would be beneficial for patients to receive a combination therapy in order to treat such conditions, and the combination therapy becomes a recommended therapy strategy.

It is already well known that the application and administration of an HMG-CoA reductase inhibitor in formulation with an angiotensin-II-receptor blocker are beneficial for the treatment of cardiovascular diseases and renal diseases. However, there is no combination drug product for the combination composition of the two drug substance, and furthermore, a combination composition, the release of which is lag time delayed considering pharmacological mechanisms including absorption, distribution and metabolism, is not yet introduced.

Information of Active Pharmaceutical Ingredients

Losartan, which is a typical agent among angiotensin-II-receptor blockers, and simvastatin, which is a typical agent among HMG-CoA reductase inhibitors, are most frequently used in combination therapy. The combination application of components contained in the composition of the present invention is reasonable, and the pharmacological effect of each component is very ideal as shown in Table 1 below.

TABLE 1

|  | Losartan | Simvastatin |
| --- | --- | --- |
| 1) Blood pressure reducing | By suppressing RAAS[1] and Vasodilating action | By preventing atherosclerosis and vasodilating actions |
|  | Combination therapy of the two components increases the antihypertensive effect of losartan and increases the lipid-reducing effect of simvastatin. | |
| 2) Chronotherapy | Excellent antihypertensive action after midnight while RAAS is active. | Pharmacological action is exhibited in the evening while lipid synthesis is most active. |
|  | When the combination of the two components is administered at about 7 p.m., the optimal antihypertensive effect is maintained at the time having the risk of development of a complication, after rising of patients having non-dipper hypertension[2]. | |

TABLE 1-continued

| | Losartan | Simvastatin |
|---|---|---|
| 3) Atherosclerosis | | Substantial lipid-reducing action |
| 4) Change of vascular walls | (1) Inhibiting the proliferation of disease cells in vascular walls. (2) Regenerating endothelial cells and maintaining the function of the cells. The administration of the two components enhances and maintains the function of the endothelial cell. | (1) anti-inflammatory action (2) cell-regenerating action |
| 5) glomerular artery | Relaxing efferent artery The combination administration of the two components enhances renal functions | Inhibiting the sclerosis of afferent and efferent arteries |
| 6) Vasodilation | Vasodilation The combination administration of the two components vasodilates further blood vessels | Vasodilation |
| 7) Inflammatatory factors MDA-CRP MCP-1 | Reducing The combination administration of the two components further reduces inflammation-causing substances | Reducing |
| 8) Insulin activity | Increasing The administration of the two components increases insulin sensitivity | Increasing, Increasing adiponectin |

[1] RAAS (Renin and Angiotensin System): one of blood pressure regulatory mechanisms in body
[2] non-dipper hypertensive patients: their blood pressure is not reduced in their sleep, unlike general hypertensive patients and having a higher risk of complications such as stroke; mostly found in the elderly, diabetic patients, cardiac hypertrophy patients etc.

1) Losartan as Angiotensin-II-Receptor Blocker and Pharmaceutical Use Thereof.

Losartan, having a chemical name of 2-butyl-4-chloro-1-[2-(1H-tetrazol-5-yl)biphenyl-4-ylmethyl]-1H-imidazole-5-methanol, is an antihypertensive agent which antagonizes the binding of angiotensin-II (AII) to a vascular receptor (AII receptor). The angiotensin II is a factor, which increases blood pressure and causes left ventricular hypertrophy, vascular hypertrophy, atherosclerosis, renal failure, stroke and the alike (see U.S. Pat. No. 5,138,069).

The angiotensin-II-receptor blocker is a drug which acts to reduce blood pressure and, at the same time, shows a wide range of effects including the prevention and treatment of renal failure, the prevention and treatment of myocardial infarction arrhythmia and heart failure, the prevention and treatment of diabetic complications, the prevention and treatment of stroke, antiplatelet effects, the prevention of atherosclerosis, the inhibition of harmful aldosterone effects, the reduction of metabolic syndrome effects, and the effect of preventing cardiovascular diseases from growing worse in a chain manner [see Clin, Exp. Hypertens., vol. 20 (1998), [p. 205-221]; J. Hypertens., vol. 13 (8) (1995), [p. 891-899]; Kidney Int., vol. 57 (2) (2000), [p. 601-606]; Am. J. Hypertens., vol. 10 (12PT2) Suppl. (1997), [p. 325-331]; Circulation, vol. 101 (14) (2000), [p. 1653-1659]; J. Hypertension., vol 17 (7) (1999), [p. 907-716]; Circulation, vol. 101 (2000), p. 2349].

The antihypertensive and renal protective effects of angiotensin-II-receptor blockers including losartan, are described in, for example, the following publications: J. Wagner et al., Effects of AT1 receptor blockade on blood pressure and the renin angiotensin system in spontaneously hypertensive rats of the stroke prone strain, Clin, Exp. Hypertens., vol. 20 (1998), p. 205-221; M. Bohm et al., angiotensin-II-receptor blockade in TGR(mREN2)27: Effects of renin-angiotensin-system gene expression and cardiovascular functions, J. Hypertens., vol. 13 (8) (1995), p. 891-899.

Other renal protective effects of angiotensin-II-receptor blockers, found in the first clinical trials, are described in the following publications: S. Andersen et al., Renoprotective effects of angiotensin-II-receptor blockade in type 1 diabetic patients with diabetic nephropathy, Kidney Int., vol. 57 (2) (2000), p. 601-606; L. M. Ruilope, Renoprotection and renin-angiotensin system blockade in diabetes mellitus, Am. J. Hypertens., vol. 10 (12PT2) Suppl. (1997), p. 325-331.

The effects of angiotensin-II-receptor blockers on endothelial dysfunction are described in the following publications: E. L. Schiffrin et al., Correction of arterial structure and endothelial dysfunction in human essential hypertension by the angiotensin receptor antagonist losartan, Circulation, vol. 101 (14) (2000), p. 1653-1659; R. M. Touyz et al., Angiotensin-II-stimulates DNA and protein synthesis in vascular smooth muscle cells from human arteries: role of extracellular signal-regulated kinases, J. Hypertension., vol 17 (7) (1999), p. 907-716; E. L Schiffrin, Vascular remodeling and endothelial function in hypertensive patients: Effect of antihypertensive therapy, Scand. Cardiovasc. J., vol. 32, Suppl. 47 (1998) p. 15-21; Prasad, Acute and Chronic angiotensin-1 receptor reverses endothelial dysfunction in atherosclerosis, Circulation, vol. 101 (2000), p. 2349.

Also, it is known that angiotensin-II-receptor blockers block AT1 receptors, but do not affect AT2 receptors, which have the effects of inhibiting growth and tissue regeneration.

2) Simvastatin as HMG-CoA Reductase Inhibitor and Pharmaceutical Use Thereof. Simvastatin is a Typical Statin-Based Lipid-Reducing Agent, which is Most Frequently Used Among HMG-CoA Reductase Inhibitors.

Simvastatin serves to strongly inhibit HMG-CoA reductase which is converted to 3-hydroxy-3-methylglutaryl-coenzyme A (HMG-CoA) into mevalonate, thus showing the effects of inhibiting the production of cholesterol in the liver and reducing low-density lipoprotein cholesterol (LDL-C) levels. Due to such effects, simvastatin is excellent in treating composite hyperlipidemia, and in treating and preventing atherosclerosis. Furthermore, it was proven through studies that the effect of reducing low-density lipoprotein cholesterol levels is highly effective against coronary heart diseases [see "Scandinavian Simvastatin Survival Study" published in the Lancet, vol. 344, (1994), p. 1383-89].

It is known that a statin-based lipid-reducing agent as an HMG-CoA reductase inhibitor is a primary drug for the prevention and treatment of heart diseases resulting from coronary artery atherosclerosis including angina or myocardial Infarction [see Lancet 1995; 346: 750-753, Am J Cardiol 1998; 82: 57T-59T, Am J Cardiol 1995; 76: 107C-112C, Hypertens Res 2003; 26: 699-704, Hypertens Res 2003; 26: 273-280.] Br Med Bull 2001; 59: 3-16, Am J Med 1998; 104 (Suppl 1): 6S-8S, Clin Pharmacokinet 2002; 41: 343-370].

Also, among HMG-CoA reductase inhibitors, simvastatin is most frequently used, and the efficacy in the treatment of coronary heart diseases and I the reduction of the mortality rate has been proven through large-scale clinical trials [see Lancet 1994; 344: 1383-1389].

This effect is because simvastatin strongly inhibits HMG-CoA reductase performing a key role in a process of synthesizing cholesterol in the liver and, at the same time, inhibits inflammation-causing factors [see "Scandinavian Simvastatin Survival Study" published in the Lancet, 1994, 344, 1383-89].

Simvastatin is a lactone-based compound, which is inactive by itself, and it primarily enters the liver, in which it changes into active its active β-hydroxyacid having lipid-reducing action. The remaining simvastatin is also metabolized in several steps by cytochrome P450 3A4 in the liver, and some of the metabolites exhibit a potent lipid-reducing effect.

Simvastatin and its β-hydroxyacid are metabolized by enzyme cytochrome P450 3A4 in the liver, and they are acting in the liver while they are partially released into the blood vessel [see Drug Metab Dispos 1990; 18: 138-145, Drug Metab Dispos 1990; 18: 476-483, Drug Metab Dispos 1997; 25: 1191-1199].

Thus, when simvastatin is used together with a drug, which is metabolized by cytochrome P450 3A4 enzyme, the metabolism of simvastatin in the liver will be inhibited, so that the blood level of simvastatin will be increased. For this reason, serious side effects such as myolysis can occur [see Clin Pharmacol Ther 1998; 63: 332-341; Clin Pharmacol Ther 1998; 64: 177-182; Physicians Desk Reference 2006 (Zocor); Pharmacol Exp Ther 1997; 282: 294-300; Pharmacol Exp Ther 1999; 290: 1116-1125; Life Sci 2004; 76: 281-292].

Accordingly, when an HMG-CoA reductase inhibitor such as simvastatin is administered together with an angiotensin-II-receptor blocker, which is metabolized by the cytochrome P450 3A4 enzyme which is required by the HMG-CoA reductase inhibitor, a special administration method should be considered.

Because the synthesis of lipid in the liver becomes active after dinner in the early evening, it has been recommended that statins be administered in the early evening [see Arterioscler Thromb 11: 816-826, Clinic Pharmacol Ther 40: 338-343].

Problem of Simple Combination Therapy

It is already well known that the application and administration of an angiotensin-II-receptor blocker together with an HMG-CoA reductase inhibitor are advantageous for the treatment of cardiovascular diseases and renal diseases. However, when an HMG-CoA reductase inhibitor such as simvastatin is used together with a drug which is metabolized by the cytochrome P450 3A4 enzyme, the metabolism of simvastatin in the liver will be inhibited, leading to an increase in the blood level of simvastatin. For this reason, side effects such as myolysis can occur. Because such fact is not well known, patients have taken such drugs without recognizing such fact.

If the two drugs administration does increase more risk rather than more benefit, the combination administration should be avoided in principle. However, an angiotensin-II-receptor blocker and an HMG-CoA reductase inhibitor, particularly losartan and simvastatin, have been prescribed together despite the risk of side effects, such as myopathy, to be likely caused by the inhibitory effect of losartan against simvastatin through completive inhibition on the same cytochrome P450 3A4 enzyme. It is because such two drugs have each advantage of the actions for the synergistic effect.

Simvastatin strongly inhibits the conversion activity to mevalonate of HMG-CoA reductase 3-hydroxy-3-methylglutaryl-coenzyme A (HMG-CoA) to mevalonate, thus showing the effects of inhibiting the production of cholesterol in the liver and reducing low-density lipoprotein cholesterol (LDL-C) levels.

For theses reason lipid-reducing effect, simvastatin should act in the liver. Meanwhile, simvastatin is a first-pass drug which is absorbed from the small intestines upon administration and enters the liver, and it mostly changes into an active type by cytochrome P450 3A4 in the liver, and then acts in the liver, and is metabolized in the liver, and excreted from the liver. The remaining simvastatin, which has not been metabolized by cytochrome P450 3A4, moves into blood to reach the whole body, and it accounts for about 5% of the administered simvastatin. An increase in the blood level of simvastatin has no connection with the therapeutic effect of inhibiting the production of cholesterol, but rather means that the risk of causing myopathies, such as myolysis, which is the side effect of simvastatin, is further increased.

Losartan, after absorbed from the small intestines, enters the liver. A portion thereof is released into blood in the form of an active losartan molecule, which then reaches the mean peak concentration in blood within 1 hour. However, the remaining portion is metabolized by two enzymes, cytochrome P450 2C9 and 3A4, in the liver, so as to be changed into losartan carboxylic acid (losartan's active metabolite) having higher activity, which then reaches the highest concentration in blood after 3-4 hours. That is, the pharmacological action of losartan is the pharmacological action of a mixture of losartan with losartan carboxylic acid (losartan's active metabolite). About 14% of the orally-administered dose of losartan is converted into the form of losartan carboxylic acid (active metabolite) by enzymes in the liver, and the active metabolite exhibits pharmacological activity more 40 times than that of losartan. The blood excretion rate is 600 mL/min for losartan and 50 mL/min for losartan carboxylic acid (active metabolite), suggesting that the active metabolite shows a slower excretion rate, and thus plays an important role in maintaining the long-lasting action time.

From this point of view, when simvastatin and losartan are administered simultaneously, the following problems will occur.

If simvastatin and losartan simultaneously enter the liver, the competitive inhibition between the two drugs in the liver is to be happening and thus the portion of simvastatin, which has not been metabolized by cytochrome P450, will be released into blood, it result in reducing the effect of the HMG-CoA reductase inhibition and increasing the risk of side effects. Meanwhile, the conversion of losartan to losartan carboxylic acid (active metabolite) will be inhibited and the effect of losartan will reduce. Therefore, if the two drugs are simultaneously co-administered, they cannot show the optimal effect because they antagonize each other [see Cytochrome P450 Drug Interaction Table, Department of Medicine, Indiana University updated 2004 Mar. 11].

Examples of Prior Art

As combination therapies for improving various disease conditions, combination therapies of HMG-CoA reductase inhibitors and angiotensin-II-receptor blockers have been suggested as follows.

International Patent Publication No. WO 95/26188 discloses a method of treatment for atherosclerosis and reducing cholesterol using an HMG-CoA reductase inhibitor and an angiotensin-II-receptor blocker. Losartan is described to be a usable angiotensin-II-receptor blocker.

International Patent Publication No. WO 97/37688 discloses a combination therapy of an HMG-CoA reductase inhibitor and an angiotensin-II-receptor blocker for treating many symptoms including hypertension and atherosclerosis.

International Patent Publication No. WO 99/11260 discloses a combination use of atorvastatin, losartan, irbesartan and valsartan for reducing blood pressure and lipid levels and treating angina and atherosclerosis in mammals.

International Patent Publication No. WO 00/45818 discloses a combination use of an HMG-CoA reductase inhibitor and an angiotensin-II-receptor blocker for improving diabetic neuropathy, specifically improving nerve conduction velocity and nerve blood flow in patients suffering from diabetes.

International Patent Publication No. WO 04/062729 discloses a combination therapy of simvastatin as an HMG-CoA reductase inhibitor, and telmisartan as an angiotensin-II-receptor blocker for the prevention or treatment of cardiovascular, cardiopulmonary, pulmonary or renal diseases.

International Patent Publication No. WO 06/040085 discloses a bilayered tablet for the prevention or treatment of cardiovascular, cardiopulmonary, pulmonary or renal diseases, which comprises simvastatin as an HMG-CoA reductase inhibitor, and telmisartan as an angiotensin-II-receptor blocker. The disclosed bilayered tablet is a combination in which simvastatin and telmisartan are simultaneously released, and it has a concept completely different from the novel inventive concept of the present invention in which the HMG-CoA reductase inhibitor is released first, such that it is metabolized first in the liver. In terms of logical or pharmacological point of view, this kind of combination therapy is thought to be inappropriate for obtaining the optimal Synergistic effects of the two drugs. This kind of therapy, when the HMG-CoA reductase inhibitor and the angiotensin-II-receptor blocker are simultaneously introduced into the liver, the metabolisms thereof by cytochrome P450 3A4 will be competitive, and thus the HMG-CoA reductase inhibitor will be released into blood without being metabolized in the liver. That is, the above said patent publications have problems in that the HMG-CoA reductase inhibitor, which should be metabolized in the liver to act in the liver, shall be released into blood without being sufficiently metabolized, resulting in the unnecessary high increase of the blood level of the simvastatin and its metabolites, which may cause myopathy.

Such simple combination product may well not be patentable due to lack of any inventiveness. Korean Patent Publication No. 2000-7002144 was rejected, because it relates to a simple combination.

A lag time delayed combination according to the present invention comprises an HMG-CoA reductase and an angiotensin-II-receptor blocker and is a novel development for the first time. The combination product of the present invention enables each of the components to exhibit the highest pharmacological effect and can reduce the side effect of each component, which may occur if the two components are simultaneously co-administered.

DISCLOSURE OF INVENTION

Technical Problem

Conception of Combination Preparation

Accordingly, the present inventors have developed a novel formulation for the first time in the world, in which the formulation can reduce side effects (such as myolysis) occurring if the two drugs are simultaneously co-administered, and in which two active pharmaceutical ingredients, from a pharmacological viewpoint, may play each full of the pharmacological effects through sufficient metabolism, and provide clinical synergistic effects by being each released at the time when each of the drugs exhibits most optimally pharmacological effect. Up to now, any type of the combination product comprising an angiotensin-II-receptor blocker and HMG-CoA reductase inhibitor in such formulation that a lag time delayed release technology is applied to one component and pharmacodynamics and pharmacokinetics of two drugs are adjusted for the synergistic effects by avoiding the antagonism in the liver.

The present invention provides a pharmaceutical combination preparation, which comprises an angiotensin-II-receptor blocker and an HMG-CoA reductase inhibitor and is most suitable for the prevention and treatment of cardiovascular, cardiopulmonary, pulmonary or renal diseases in metabolic syndrome or insulin resistance patients and patients suspected of having diabetes or prediabetes.

The present invention relates to a combination composition of an angiotensin-II-receptor blocker and an HMG-CoA reductase inhibitor. That is, the present invention relates to a drug delivery system for oral administration, which is most suitable for the fully synergistic effects of each active ingredients in body. In other words, the present invention relates to a drug delivery system designed such that each drug has a specific release rate, and such that it can show the most ideal therapeutical benefits, when it is absorbed in body.

If the HMG-CoA reductase inhibitor and the angiotensin-II-receptor are released at different times so as to inhibit the simultaneous transfer of the drugs into the liver and to inhibit the competitive antagonism occur between for enzymes in the liver, the effect of each of the HMG-CoA reductase inhibitor and the angiotensin-II-receptor blocker can be maximized, and the side effects of the HMG-CoA reductase inhibitor can also be reduced. Thus, it may be a highly preferable method to have the HMG-CoA reductase inhibitor and the angiotensin-II-receptor released at different times.

That is, it was already found through clinical studies that the use of the angiotensin-II-receptor blocker showing a blood pressure-reducing effect, together with the HMG-CoA reductase inhibitor as an agent for treating coronary arterial diseases, would show a synergistic effect against coronary heart diseases. However, when the two drugs are co-administered at the same time, they can antagonistically inhibit each other or can cause side effects, because the competitive antagonism of the angiotensin-II-receptor blocker and the HMG-CoA reductase inhibitor for hepatic metabolic enzymes can occur. Thus, a delayed-release combination composition capable of preventing competitive antagonism between drugs in the liver is developed, it can meet the desirable therapeutic needs, because it shows a clinical synergistic effect through the combination product of two drugs, which releases each components at the proper time to be absorbed and metabolized in the liver so as to avoid any antagonism between the two drugs. Also, because the release of two drugs at different times is possible by taking a single formulation for oral administration once a day at a specific time, it is convenient to administer the drugs to patients, thus increasing therapeutically compliance.

However, a combination composition, which can solve such clinical problems, has not yet been developed. According to the present invention, the problems, which can occur in pharmacological mechanisms, can be solved by administering a combination composition enabling intended lag time delayed-release, only once a day, and such that each of two drugs can be released at the optimal time based on the xenobiotics of the two drugs.

Because the synthesis of cholesterol actively progresses at night, it is most effective to administer the HMG-CoA reductase inhibitor in the evening. Also, because the angiotensin-II-receptor blocker has a duration of action of 24 hours, it is most effective to take the angiotensin-II-receptor blocker in the evening, such that it is active in the morning when blood pressure reaches the highest level. Therefore, the two drugs should be administered in the evening, and patients are likely to simultaneously take the two drugs, which are separately present as single drugs. However, patients are opting to simultaneously take the two drugs as usually prescribed.

Such medication would cause competitive inhibition between drugs on cytochrome P450 3A4 in the liver to reduce the effects of the drug and to increase the side effects of the drugs.

Therefore, when two drugs are to be administered, it is mandatory to administer the HMG-CoA reductase inhibitor at first and then to administer the angiotensin-II-receptor blocker after a given time, but the knowledge of such medication method is not easily provided to patients.

Furthermore, patients who would take such two drugs are mostly elderly who are always poor and incorrect in the compliance.

Accordingly, the present inventors have made efforts to solve the above-mentioned problems and performed clinical tests for comparing the simultaneous administration of the HMG-CoA reductase inhibitor, represented by simvastatin, and the angiotensin-II-receptor blocker, represented by losartan, with the administration of the two drugs at different times, in order to develop a drug delivery system designed such that the release rates of the drugs can be lag time delayed based on the absorption in body, metabolism and action mechanism of each drug so as to prevent the antagonism between the drugs, thus preventing or reducing side effects, and such that the synergistic effect of the drugs can be maximized when they are administered together. As a result, the present inventors have found that, when the HMG-CoA reductase inhibitor and the angiotensin-II-receptor blocker are administered at different times, the onset and safety of the drugs are significantly improved compared when the drugs are administered simultaneously.

That is, the present inventors have found that, when the combination product of the present invention is orally administered, a clinical synergistic effect of the HMG-CoA reductase inhibitor and the angiotensin-II-receptor blocker can be provided, and the competitive antagonism between the two drugs can be avoided through the lag time delayed release of the drugs, and can maximize the efficacy and can minimize the side effects of the drugs, and can improve the compliance of patients. Moreover, the combination product of this present invention is a single tablet for once a day in the evening.

It is the object of the present invention to provide a drug delivery system in which the release of one of two active ingredients is individually lag time delayed so as to provide pharmacological advantages, as well as a preparation method thereof. The dissolution of the angiotensin-II-receptor blocker is delayed for 3-4 hours of initial release, and preferably for more than 4 hours of initial release. When the HMG-CoA reductase inhibitor is released ahead of the angiotensin-II-receptor blocker, it will absorbed in the small intestines ahead of the angiotensin-II-receptor blocker and will be bound to cytochrome P450 3A4 in the liver, so that the HMG-CoA reductase inhibitor will be metabolized in the liver to inhibit the biosynthesis of cholesterol. The angiotensin-II-receptor blocker, released 3-4 hours (preferably more than 4 hours) after the HMG-CoA reductase inhibitor is absorbed, will be metabolized by the regenerated cytochrome P450 3A4, so that it will converted to the active metabolites of the angiotensin-II-receptor blocker metabolite which shows blood pressure-reducing effects.

Another object of the present invention is to provide a dosage form for treating hypertension, coronary heart diseases and related conditions, which contains an angiotensin-II-receptor blocker or pharmaceutically acceptable salt thereof and an HMG-CoA reductase inhibitor, and in which the HMG-CoA reductase inhibitor is released immediately and the angiotensin-II-receptor blocker or a pharmaceutically acceptable salt thereof is released slowly.

Technical Solution

The present invention provides a lag time delayed-release combination containing, as active ingredients, an angiotensin-II-receptor antagonist and an HMG-CoA reductase inhibitor, together with a pharmaceutically acceptable excipient, the combination composition comprising: a lag time delayed-release portion comprising the angiotensin-II-receptor antagonist as an active pharmaceutical ingredient; and an immediate-release portion comprising the HMG-CoA reductase inhibitor as an active ingredient.

When the drug delivery system of the present invention is orally administered, the HMG-CoA reductase inhibitor is released immediately, such that more than 80% of the drug is dissolved within 1 hour, and the release of the angiotensin-II-receptor blocker in the gastrointestinal tracts is sufficiently delayed, such that the dissolution rate thereof up to a total of 4 hours after oral administration does not exceed 40%. Preferably, the HMG-CoA reductase inhibitor is released, such that more than 90% of the drug is dissolved within 1 hour, and the release of the angiotensin-II-receptor blocker in the gastrointestinal tracts is sufficiently delayed, such that the dissolution rate thereof up to a total of 4 hours after oral administration does not exceed 30%. More preferably, the release of the drugs is lag time delayed such that the angiotensin-II-receptor is substantially released after 4 hours from the start of dissolution of the HMG-CoA reductase inhibitor.

Hereinafter, the present invention will be described in detail.

The present invention relates to a combination preparation designed based on so-called "chronotherapy" and "xenoibotics", in which drugs are administered to be released at different time such that the release of one drug component can be lag time delayed to a specific release rate. The combination preparation of this present invention comprises, as active drugs, an angiotensin-II-receptor blocker and an HMG-CoA reductase inhibitor, both of which are affected by the same cytochrome P 450 enzymes in which the drugs have different release rates, such that the antagonism between the drugs can be prevented so as to reduce the side effects of each drugs, to achieve the synergistic effects and to improve the convenience and compliance for the patients.

Hereinafter, the pharmaceutical combination preparation of the present invention, which comprises the angiotensin-II-receptor blocker and the HMG-CoA reductase inhibitor, will be described in detail.

The combination preparation of the present invention comprises, as active ingredients, an angiotensin-II-receptor blocker and an HMG-CoA reductase inhibitor. The angiotensin-II-receptor blocker may be selected from components, which are metabolized by cytochrome P450 enzymes, and specific examples thereof include losartan, valsartan, irbesartan, candesartan, telmisartan, eprosartan, olmesartan, and pharmaceutically acceptable salts thereof, but the scope of the present invention is not limited to these angiotensin-II-receptor blockers. Preferably, losartan or its pharmaceutically acceptable salts can be used. Also, a typical example of a pharmaceutically acceptable salt of losartan is losartan potassium. Because the angiotensin-II-receptor blocker is used in an amount of 5-1200 mg per day for adults (adult males weighing 65-75 kg), it is used in an amount of 5-1200 mg, and preferably 8-600 mg in the combination product of this invention (having a total weight of 200-1010 mg).

As the angiotensin-II-receptor blocker showing blood pressure-reducing effects, losartan will be described by way of example herein, but the scope of the present invention is not limited thereto.

Also, the pharmaceutical combination composition of the present invention comprises the HMG-CoA reductase inhibitor as an active ingredient. and the HMG-CoA reductase inhibitor is an inactive substance, but it performs lipid-reducing action, after it is converted into active its β-hydroxyacid by esterase and converted into an active metabolite by cytochrome P450 3A4 in the liver. Specific examples thereof may include simvastatin, lovastatin, atorvastatin, pitavastatin, rosuvastatin, fluvastatin, pravastatin, and pharmaceutically acceptable salts thereof. Preferably, it can be selected from simvastatin, lovastatin, atorvastatin, and pharmaceutically acceptable salts thereof. More preferably, simvastatin or its pharmaceutically acceptable salt can be used. Although simvastatin is described by way of example herein, the scope of the present invention is not limited thereto. Because this HMG-CoA reductase inhibitor is used in an amount of 5-160 mg per day for adults, it is used in an amount of 5-160 mg, and preferably 5-80 mg, in the inventive combination composition (having a total weight of 200-1010 mg).

When simvastatin, HMG-CoA reductase inhibitor and losartan, angiotensin-II-receptor simultaneously enter the liver, the competitive inhibition between the two drugs in the liver will occur. Thus the portion of simvastatin, which has not been metabolized by cytochrome P450, will be released into blood to reduce the effect of the HMG-CoA reductase inhibitor and to increase the risk of causing side effects. Also, the conversion of losartan to losartan carboxylic acid (active metabolite) will be inhibited to reduce its activity. Therefore, if such two drugs are simultaneously co-administered, they cannot show the optimal effect of two drugs, because they antagonize each other.

In order to solve the above-described problem in such a way that the angiotensin-II-receptor inhibitor as an active ingredient may not interfere with the HMG-CoA reductase inhibitor in the liver, the present invention is technically designed and characterized in that the HMG-CoA reductase inhibitor is formulated into an intermediate-release portion to be dissolved first so as to be absorbed first from the small intestines, and the angiotensin-II-receptor inhibitor is formulated into a lag time delayed-release portion, to be absorbed 3-4 hours later than the HMG-CoA reductase inhibitors.

The comparison between the functional combination preparation of the resent invention and the simple simultaneous co-administration may be described as shown in Table 2 below.

TABLE 2

| | Simultaneously co-administration | Functional combination product of the present invention |
|---|---|---|
| 1) Dosage time | Administered mainly at about 7 a.m. | Administered at about 7 p.m. |
| 2) Dissolution and absorption of two components | Dissolved and absorbed simultaneously in the morning | Simvastatin: dissolved and absorbed at 7 p.m. Losartan: dissolved and absorbed at 11 p.m. |
| 3) prime time period of antihypertensive action | Between 10 a.m. and 10 p.m. | Between 10 p.m. and 10 a.m. of the next day |
| 4) Blood pressure control in non-dipper hypertension patients | Unsuitable | Effective for non-dipper hypertension patients having a high risk of development of complications |
| 5) Preventive effect at the time (between 5 a.m. and 11 a.m.) showing the most frequent risk-prevalence of cardiovascular complications | (1) If losartan is administered At 7 a.m., losartan will show the peak blood concentration from 1 p.m., being decreased from 1 am. Thus, it is unsuitable for non-dipper hypertension patients, who should be more strongly controlled from 1 am. Further, during the the prime Time when the cardiovascular complication are mostly happened (between 5 a.m. and 11 a.m.) the antihypertensive action of losartan becomes weaker. | (1) When the functional combination product of this invention is administered at 7 p.m., simvastatin will be released first. Thus, simvastatin can sufficiently act at the time when lipid synthesis is active. (2) Because losartan is dissolved and released into the liver at 3-4 hours after simvastatin is metabolized by enzymes in the liver, losartan is also sufficiently metabolized by enzymes in the liver and released into blood, so that it can exhibit a sufficient |

TABLE 2-continued

| | Simultaneously co-administration | Functional combination product of the present invention |
|---|---|---|
| 6) Interaction between two components | (2) Simvastatin should be principally administered in the evening when lipid metabolism is mainly activated. Therefore, such two drugs should be administered in the evening but not in the morning Competitive binding Because the two components are released simultaneously, they are metabolized by the same cytochrome P450 3A4 enzyme in the liver, and thus competitively antagonize each other. Cytochrome P450 3A4: 1) It changes inactive simvastatin to an active component and enables active simvastatin to act in the liver. 2) It increases the activity of active losartan by more than 40 times and enables active losartan to exhibit antihypertension action in blood. | blood pressure-reducing effect in non-dipper hypertension patients showing an increase in blood pressure at dawn, and at the time (between rising and 11 a.m.) having the risk of development of complications. Competitive binding Because the two components are released with an interval of 3-4 hours, they do not compete with each other in metabolism by cytochrome P450 3A4 enzyme in the liver and are sufficiently activated in the liver. |

Advantageous Effects

As described above, the present invention provides a pharmaceutical combination designed based on chronotherapy and xenobiotics for maximizing therapeutic effects and for preventing or reducing side effects, which can occur upon the co-administration of two drugs. The combination product of this invention comprises, as active ingredients, an angiotensin-II-receptor blocker and an HMG-CoA reductase inhibitor, which are affected by the same cytochrome P450-enzymes. At the same time, the combination comprises different lag time delayed-release pharmaceutically exceptable excipients, which can control the time when the active ingredients are released in body, such that the active ingredients can be released at different times in body. Accordingly, the combination product of this invention is more useful in pharmacological, clinical, scientific and economic terms in the prevention or treatment of hypertension having complication such as cardiovascular, cardiopulmonary, pulmonary or renal diseases, metabolic syndrome including insulin resistance, diabetes or prediabetes, compared with the simultaneous co-administration of the two drug components.

Also, according to the present invention, the combination is formulated such that the drugs have different release rates. Thus, the antagonism between the drugs and the side effects of the drugs can be prevented or reduced and the synergistic effect of the drugs can be obtained.

In addition, according to the present invention, the combination can be administered once a day, and thus it is easy to instruct patients on medication and to administer the combination product of this invention.

The advantages of the novel combination preparation of the present invention over the simultaneous co-administration may be summarized as in Table 3 below.

TABLE 3

The novel combination product of this present invention has the following advantages And benefits;

1) An excellent effect of lowering blood pressure.
2) An excellent effect of lowering synthesis of cholesterol . . .
3) An excellent preventive action against endothelial dysfunctions from being worsened TABLE 3-continued The novel combination product of this present invention has the following advantages And benefits;

4) The optimal effect at the time of the most frequent prevalence of the cardiovascular risky complications.
5) An excellent efficacy in treatment of the hypertension of non-dipper patients.
6) Significant reduction of insulin resistance in hypertensive diabetes.
7) Reduction of time to be consumed for the patient instruction on medication, and realization of the right way of multiple prescription method

MODE FOR INVENTION

Figure 1:
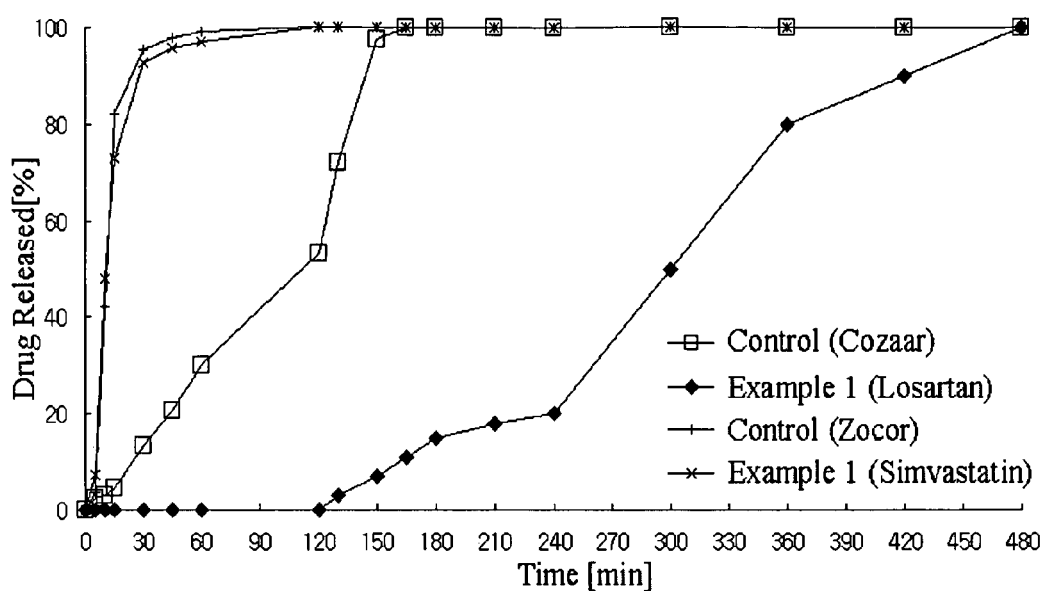
FIG. 1 is a diagram showing the comparative dissolution profiles of a lag time delayed-release formulation of losartan/simvastatin, prepared in Example 1, and the losartan and simvastatin components of single drugs, Cozaar® and Zocor®, as control groups.

The novel pharmaceutical combination composition of the present invention comprises: a lag time delayed-release portion comprising an angiotensin-II-receptor inhibitor or a pharmaceutically acceptable salt and pharmaceutical acceptable excipients; and an immediate release portion comprising an HMG-CoA reductase inhibitor or a pharmaceutically acceptable salt thereof and desired excipients, wherein the two portions are physically separated or divided from each other, such that the two drugs may have different release rates. The above-described immediate release portion and lag time delayed-release portion can be embodied in various formulations.

That is, the lag time delayed-release portion can be coated with a release-controlling material according to a conventional method, and the coated particles or granules thus obtained, and the particles or granules of the immediate release portion can be compressed into a tablet or filled in a capsule.

This pharmaceutical combination composition of the present invention exhibits advantageous effects, when it is administered between 5 p.m. and 10 p.m. once a day.

The lag time delayed-release portion of the present invention comprises an angiotensin-II-receptor blocker, represented by losartan, and a material for controlling the release of the angiotensin-II-receptor blocker, the release controlling material being a component selected from an enteric polymer, a water-insoluble polymer, a hydrophobic compound and a hydrophilic polymer. The release controlling material of the lag time delayed-release portion can be used in an amount of 10-500 parts by weight based on 100 parts by weight of angiotensin-II-receptor blocker. If the amount of use of the release-controlling material is below the reduce limit of the range, it cannot achieve sufficient release-controlling, and if the amount of use of angiotensin-II-receptor blocker exceeds the upper limit of the range, the drug release will be delayed, and thus a significant clinical effect cannot be obtained.

The enteric polymer may be one or a mixture of two or more selected from polyvinyl acetate phthalate, methacrylic acid copolymers, hydroxypropylmethylcellulose phthalate, shellac, cellulose acetate phthalate, cellulose propionate phthalate, Eudragit L and Eudragit S. Preferred is hydroxypropylmethylcellulose phthalate.

The water-insoluble polymer may be one or a mixture of two or more selected from polyvinyl acetate, polymethacrylate copolymers, such as poly(ethylacrylate, methylmethacrylate) copolymers and poly(ethylacrylate, methyl methacrylate and trimethylaminoethylmethacrylate) copolymers, ethyl cellulose and cellulose acetate, which are pharmaceutically acceptable salts.

The hydrophobic compound may be selected from fatty acids, fatty acid esters, fatty acid alcohols, waxes and inorganic materials. Specifically, it may be one or a mixture of two or more selected from: fatty acids or fatty acid esters including glyceryl palmitostearate, glyceryl stearate, glyceryl behenate, cetyl palmitate, glyceryl monooleate and stearic acid; fatty acid alcohols including cetostearyl alcohol, cetyl alcohol and stearyl alcohol; waxes including Carnauba wax, beewax and microcrystalline wax; and inorganic materials including talc, precipitated calcium carbonate, dibasic calcium phosphate, zinc oxide, titanium oxide, kaolin, bentonite, montmorillonite and veegum.

The hydrophilic polymer may be selected from saccharides, cellulose derivatives, gums, proteins, polyvinyl derivatives, polymethacrylate copolymers, polyethylene derivatives and carboxyvinyl polymers. Specifically, it may be one or a mixture from among: saccharides including dextrin, polydextrin, dextran, pectin and pectin derivatives, alginate, polygalacturonic acid, xylan, arabinoxylan, arabinogalactan, starch, hydroxypropyl starch, amylose and amylopectin; cellulose derivatives including hydroxypropylmethyl cellulose, hydroxypropyl cellulose, hydroxymethyl cellulose, hydroxyethyl cellulose, methyl cellulose, carboxymethyl cellulose sodium, hydroxypropyl methylcellulose acetate succinate, and hydroxyethylmethylcellulose; gums including guar gum, locust bean gum, tragacanth, carrageenan, acacia gum, Arabic gum, gellan gum, and xanthan gum; proteins including gelatin, casein and zein; polyvinyl derivatives including polyvinyl alcohol, poly(vinyl pyrrolidone) and polyvinylacetaldiethylaminoacetate; polymethacrylate copolymers including poly(butyl methacrylate, (2-dimethylaminoethyl)methacrylate, methylmethacrylate) copolymers, poly(methacrylic acid, methylmethacrylate) copolymers, and poly(methacrylic acid, ethylacrylate) copolymers; polyethylene derivatives including polyethylene glycol and polyethylene oxide; and carboxyvinyl polymers such as carbomer.

Within a range not to impair the effects of the present invention, pharmaceutically acceptable dilutes such as starch, microcrystalline cellulose, lactose, glucose, mannitol, alginate, alkaline earth metal salts, clay, polyethylene glycol and dicalcium phosphate may be used, and lubricants including talc, alkaline-earth metal stearate such as calcium stearate, magnesium stearate or zinc stearate, lauryl sulfate, hydrogenated vegetable oil, sodium benzoate, sodium stearyl fumarate, glyceryl monostearate and polyethyleneglycol 4000 may be used, but the scope of additives for use in the present invention is not limited thereto.

The lag time delayed-release portion of the novel combination product of this present invention consists of a discontinuous phase comprising of particles or granules obtained by mixing, granulating or coating an angiotensin-II-receptor blocker, a lag time delayed-controlling material and a pharmaceutically acceptable conventional excipient.

The immediate release portion of the inventive combination composition can be prepared in the form of particles or granules by subjecting an HMG-CoA reductase inhibitor (represented by simvastatin), as an active ingredient, together with a pharmaceutically acceptable excipient to conventional processes for producing oral solid drugs, such as mixing, kneading, drying and granulation. If the fluidity of the simvastatin mixture is good such that it can be directly compressed into tablets, the composition can be obtained through a mixing process, and if the fluidity is poor, the composition can be obtained in the form of granules by compression, granulation and sieving. In this way, a continuous phase consisting of the immediate release portion can be obtained.

A two-phase matrix formulation for oral administration comprising the lag time delayed-release portion and the immediate release portion can be prepared by adding pharmaceutically acceptable additives to the compositions constituting the above-prepared lag time delayed-release portion and immediate release portion and compressing the mixture into tablets or filling the mixture in capsules.

For example, it is possible to prepare formulations, such as a two-phase matrix tablet having two granular phases, a multilayered tablet, a dry-coated tablet, and a capsule in which two granular phases consisting of the lag time delayed-release portion and the immediate release portion are filled. Also, it is possible to prepare a double layer tablet, which has a core layer of angiotensin-II-receptor blocker showing delayed release and an outer layer of HMG-CoA reductase inhibitor showing immediate release.

However, a formulation, which can be prepared according to the present invention, is not limited to the two-phase matrix tablet which exists as a single tablet and in which a discontinuous phase comprising of the lag time delayed-release angiotensin-II-receptor blocker is located within a continuous phase comprising the immediate release HMG-CoA reductase inhibitor.

That is, a multi-layered tablet for oral administration, which shows immediate release and lag time delayed-release according to each layer, can be obtained by mixing granules which constitute the lag time delayed-release portion and the immediate release portion with pharmaceutical excipients, and compressing the mixture using a multiple tableting machine into a two-layered or three-layered tablet having parallel layers.

Also, a tablet for oral administration, which has a slow release layer in a core and comprises an immediate release layer covering the surface of the core, can be obtained by mixing a granule constituting the lag time delayed-release portion with a pharmaceutical excipient, tableting the mixture to form a core tablet, mixing a granule constituting the immediate release portion with a pharmaceutical excipient, and compressing the mixture onto the surface of the core tablet to form an outer layer.

Moreover, a two-phase lag time delayed-release capsule formulation for oral administration can also be obtained by mixing granules constituting the lag time delayed-release portion and the immediate release portion with pharmaceutical excipients, and, if necessary, filling the mixture in a capsule.

Pharmaceutically acceptable additives to the active ingredient of the immediate release portion containing diluents, binders, disintegrants, lubricants, stabilizers, colorants and fragrance, and are preferably used in an amount of 100-3,000 parts by weight based on 100 parts by weight of the HMG-CoA reductase inhibitor. Within a range not to impair the effects of the present invention, as pharmaceutically acceptable diluents, starch, microcrystalline cellulose, lactose, glucose, mannitol, alginate, alkaline earth metal salts, clay, polyethylene glycol and dicalcium phosphate may be used. Examples of binders may include starch, microcrystalline cellulose, highly dispersible silica, mannitol, lactose, polyethylene glycol, polyvinyl pyrrolidone, hydroxypropyl methylcellulose, hydroxypropylcellulose, natural gum, synthetic gum, Copovidone and gelatin. Examples of disintegrants may include starches such as sodium starch glycolate, corn starch, potato starch pregelatinized starch or modified starch, clays such as bentonite, montmorillonite or veegum, microcrystalline cellulose, low-substitution hydroxypropylcellulose, hydroxypropylcellulose, sodium alginate, cross-linked cellulose such as croscarmellose sodium, gums such as guar gum or xanthan gum, crosslinked polymers such as crospovidone, and materials such as sodium bicarbonate or citric acid. These disintegrants may be used alone or in a mixture of two or more. Examples of lubricants may include talc, magnesium stearate, alkaline metal stearates such as calcium or zinc stearate, lauryl sulfate, hydrogenated vegetable oil, sodium benzoate, sodium stearyl fumarate, glyceryl monostearate and polyethyleneglycol 4000. Examples of stabilizers may include ascorbic acid, citric acid, butylatyed hydroxyanisole, butylated hydroxytoluene and tocopherol derivatives. In addition, pharmaceutically acceptable additives selected from colorants, fragrances and the like may be used in the present invention.

As such additives, microcrystalline cellulose, starch glycolate sodium, colloidal silica, magnesium stearate and the like were used in Examples of the present invention, but the scope of the present invention is not limited thereto, and said additives may be used in conventional amounts, which can be suitably selected by those skilled in the art.

In said formulation, if necessary, a film coating layer may be formed on the outer surface of the tablet. That is, the novel formulation of this present invention comprising of the angiotensin-II-receptor blocker and the HMG-CoA reductase inhibitor may also be used in the form of a core tablet having no coating layer, and if a coating layer is formed on the surface of the tablet containing said active ingredients so as to form a coated tablet, the stability of the active ingredients can be further ensured. The coating layer can be formed according to a suitable method selected from methods capable of forming the coating layer on the surface of the tablet layer, and examples of such methods include a fluidized bed coating method and a pan coating method. The pan coating method is preferably used.

The coating layer can be formed using a coating agent, a coating aid or a mixture thereof. Specifically, as the coating agent in the coating layer, one or a mixture of one or more selected from cellulose derivatives, sugar derivatives, polyvinyl derivatives, waxes, fats and gelatin may be used, and as the coating aid, one or a mixture of two or more selected from polyethylene glycol, ethyl cellulose, glycerides, titanium dioxide and diethyl phthalate may be used.

When the coated tablet is prepared, the coating layer is preferably included in an amount of 0.5-15 wt % based on the total weight of the tablet.

The above-described drug delivery system of the present invention comprises of the composition containing the angiotensin-II-receptor blocker as active ingredients and the HMG-CoA reductase inhibitor. Accordingly, because it is administered only one time in the evening, administration of dosage is very simple compared to the case in which single formulations containing the active ingredients, respectively, are administered simultaneously. Also, because the antagonism between the drugs does not happen, side effects resulting from the antagonism can be reduced or eliminated. In addition, the drugs show a synergistic effect on blood pressure control and lipid control at the same time.

The results of comparative clinical tests conducted to comparative test with simultaneous administration are as follows.

In a control group, a commercially available angiotensin-II-receptor blocker (50 mg losartan potassium) and a commercially available HMG-CoA reductase inhibitor (20 mg simvastatin) were simultaneously administered. In a test group, the drugs were administered at different times, such that the release times of the drugs were the same as in the composition provided in Example of the present invention, and thus the effects of the drugs were the same as those of the inventive composition. As a result, it was observed that, when the angiotensin-II-receptor blocker and the HMG-CoA reductase inhibitor were administered at different times, the efficacy and safety of the drugs were significantly improved compared to the simultaneous administration group, and that a change in the concentration of the drugs in blood was consistent with a change in the clinical efficacy and safety thereof.

The present inventors have conducted studies on a pharmaceutical composition using such a drug delivery system and, as a result, found that the pharmaceutical composition could exhibit the above-described effects.

That is, the drug delivery system of the present invention can be suitably used for the prevention or treatment of hypertension having or not having complication such as cardiovascular, cardiopulmonary, pulmonary or renal disorders, acing metabolic syndromes including insulin resistance, diabetes or prediabetes.

Hereinafter, the present invention will be described in further detail with reference to the following examples. However, the scope of the present invention is not limited to these examples.

Examples 1 to 13

Preparation of Inner-Core Tablets

1) Preparation of Losartan Lag Time Delayed-Release Core Tablets

To prepare losartan lag time delayed-release core tablets, as shown in Tables 4 and 5, losartan potassium, microcrystalline cellulose, pregelatinized starch, Copovidone and Aerosil 200 were sieved through No. 35 sieve and mixed with each other in a high-speed mixer for 5 minutes to prepare a mixture. Magnesium stearate was mixed with the mixture for 4 minutes. The resulting mixture was compressed into core tablets using a rotary tableting machine (MRC-33, Sejong Machinery Co., Korea). The core tablets thus prepared were placed in a Hi-coater (SFC-30N, Sejong Machinery Co., Korea), in which lag time delayed-release core tablet products having the compositions and contents shown in Tables 4 and 5 were prepared.

2) Preparation of HMG-CoA Reductase Inhibitor Immediate Release Layer

To prepare an HMG-CoA reductase inhibitor layer, in Example 1, HMG-CoA reductase inhibitor simvastatin and excipients including microcrystalline cellulose, lactose, corn starch and starch glycolate sodium, were sieved through No. 35 sieve and mixed with each other in a high-speed mixer. Meanwhile, hydroxypropylcellulose and citric acid were dissolved in water to prepare a binder solution. The binder solution was placed in the high-speed mixer with said mixture and kneaded. After completion of the kneading process, the kneaded material was granulated through No. 18 sieve using an oscillator, and the granules were dried in a hot-water dryer at 60° C. After completion of the drying process, the granules were sieved through No. 20 sieve. Butylated hydroxyanisole was mixed with the sieved material in a double cone mixer. Magnesium stearate was finally mixed with the mixture in the double cone mixer.

In Examples 2 to 13, immediate release products having the compositions and contents shown in Tables 4 and 5 were prepared in the same manner as described above.

3) Tableting and Coating

A press tableting machine (RUD-1: Kilian) was used to prepare dry-coated tablets, having the losartan-containing core tablet as a core layer and the simvastatin-containing composition as an outer layer. Meanwhile, hydroxypropylcellulose 2910, titanium oxide and talc were dissolved and dispersed in 132 mg of ethanol and 33 mg of purified water to prepare a coating solution. Said dry-coated tablets were placed in a Hi-coater (SFC-30N, Sejong Machinery Co., Korea), in which the tablets were then coated with the coating solution, thus preparing dry-coated tablets.

Examples 14 to 17

Preparation of 2-Phase Matrix Tablets

1) Preparation of Losartan Lag Time Delayed-Release Granules

To prepare losartan lag time delayed-release granules in Example 15, losartan potassium, microcrystalline cellulose, crosslinked polyvinylpyrrolidone and sodium chloride were sieved through No. 35 sieve and mixed with each other in a high-speed mixer for 5 minutes to prepare a mixture. Meanwhile, hydroxypropylcellulose was dissolved in purified water to prepare a binder solution. The binder solution was added to the mixture, which was then kneaded, granulated and dried. The dried material was placed in a fluidized bed coater. Meanwhile, cellulose acetate (32% acetyl group), cellulose acetate (39.8% acetyl group) and hydroxypropylcellulose were dissolved and dispersed in 220 mg of ethanol and 980 mg of methylene chloride to prepare a coating solution. The dried granules were coated with the coating solution in the fluidized bed coater (GPCG-1, Glatt, Germany), thus preparing losartan delayed-release granules.

In Examples 14, 16 and 17, delayed-release granules having the compositions and contents shown in Table 5 below were prepared according to the same method as described above.

2) Preparation of Simvastatin Immediate Release Granules

To prepare simvastatin immediate release granules, as shown in Table 5 below, simvastatin, microcrystalline cellulose and D-mannitol were sieved through No. 35 sieve and mixed with each other in a high-speed mixer. Meanwhile, hydroxypropylcellulose and citric acid were dissolved in water to prepare a binder solution, which was then kneaded with said mixture. After kneading, the kneaded material was granulated through No. 18 sieve using an oscillator, and the granules were dried in a hot-water dryer at 60° C. After drying, the granules were sieved through No. 20 sieve. The sieved material was mixed with butylated hydroxyanisole.

3) Post-Mixing, Tableting and Coating

The above-prepared losartan delayed-release granules and simvastatin immediate release granules were mixed with each other in a double cone mixer. The mixture was mixed with starch glycolate sodium and finally mixed with magnesium stearate. The resulting mixture was compressed into tablets using a rotary tableting machine (MRC-33, Sejong Machinery Co., Korea). Meanwhile, hydroxypropylmethylcellulose 2910, hydroxypropylcellulose, titanium oxide and talc were dissolved and dispersed in 64.8 mg of ethanol and 16.2 mg of purified water to prepare a coating solution. Said tablets were coated with the coating layer in a Hi-coater (SFC-30N, Sejong Machinery Co., Korea) to form a film coating layer, thus preparing two-phase matrix tablets.

Examples 18 to 27

Preparation of Multilayered Tablets

1) Preparation of Lag Time Delayed-Release Layer of Angiotensin-II-Receptor Blocker To prepare a lag time delayed-release layer of angiotensin-II-receptor blocker, in Example 18, angiotensin-II-receptor blocker losartan potassium and excipients including microcrystalline cellulose, crosslinked polyvinylpyrrolidone and sodium chloride, were sieved through No. 35 sieve and mixed with each other in a high-speed mixer for 5 minutes to prepare a mixture. Meanwhile, hydroxypropylcellulose was dissolved in purified water to prepare a binder solution. The binder solution was added to the mixture, which was then kneaded, granulated and dried. The dried granules were placed in a fluidized bed coater. Meanwhile, cellulose acetate (32% acetyl group), cellulose acetate (39.8% acetyl group) and hydroxypropylmethylcellulose were dissolved in 220 mg of ethanol and 980 mg of methylene chloride to prepare a coating solution. Said granules were coated with the coating solution in the fluidized bed coater (GPCG-1, Glatt, Germany). After completion of the coating process, the granules were mixed with magnesium stearate for 4 minutes, thus preparing a losartan lag time delayed-release layer.

In Examples 19 to 27, lag time delayed-release layers having the compositions and contents shown in Tables 5 and 6 were prepared according to the same method as described above.

2) Preparation of HMG-CoA Reductase Inhibitor Immediate Release Layer

In order to prepare an HMG-CoA reductase inhibitor layer, in Example 9, HMG-CoA reductase inhibitor simvastatin and excipients including microcrystalline cellulose and D-mannitol, were sieved through No. 35 sieve and mixed with each other in a high-speed mixer. Meanwhile, hydroxypropylcellulose and citric acid were dissolved in water to prepare a binder solution. The binder solution was added to the mixture, which was then kneaded. The kneaded material was granulated through No. 18 sieve using an oscillator, and the granules were dried in a hot-water dryer at 60° C. After drying, the granules were sieved through No. 20 sieve. The sieved material was mixed with butylated hydroxyanisole and starch glycolate sodium and finally mixed with magnesium stearate in a double cone mixer.

In Examples 19 to 27, immediate release layers having the compositions and contents shown in Tables 5 and 6 were prepared according to the same method as described above.

3) Tableting and Coating

A multilayer tableting machine (MRC-37T, Sejong Machinery Co., Korea) was used. The simvastatin-containing composition was placed in a first powder feeder, and the losartan delayed-release layer composition was placed in a second powder feeder. The compositions in the feeders were compressed into tablets in conditions in which interlayer incorporation could be minimized Meanwhile, hydroxypropylmethylcellulose 2910, hydroxypropylcellulose, titanium oxide and talc were dissolved and dispersed in 64.8 mg of ethanol and 16.2 mg of purified water to prepare a coating solution. Said tablets were coated with the coating solution in a Hi-coater (SFC-30N, Sejong Machinery Co., Korea) to form a coating layer, thus preparing multilayered extended-release tablets.

Examples 28 and 29

Preparation of Capsules

1) Preparation of Losartan Lag Time Delayed-Release Granules

In order to prepare losartan lag time delayed-release granules, in Example 28, losartan potassium, microcrystalline cellulose, crosslinked polyvinylpyrrolidone and sodium chloride were sieved through No. 35 sieve and mixed with each other in a high-speed mixer for 5 minutes to prepare a mixture. Meanwhile, hydroxypropylcellulose was dissolved in purified water to prepare a binder solution, which was then added to the mixture. The resulting mixture was kneaded, granulated and dried. The dried granules were placed in a fluidized bed coater. Meanwhile, cellulose acetate (32% acetyl group), cellulose acetate (39.8% acetyl group) and hydroxypropylmethylcellulose were dissolved in 220 mg of ethanol and 980 mg of methylene chloride to prepare a coating solution. Said granules were coated with the coating solution in the fluidized bed coater (GPCG-1, Glatt, Germany), thus preparing losartan lag time delayed-release granules.

In Example 29, losartan lag time delayed-release granules having the composition and content shown in Table 6 were prepared according to the same method as described above.

2) Preparation of Simvastatin Immediate Release Granules

In order to prepare simvastatin immediate release granules, in Example 28, simvastatin, microcrystalline cellulose and D-mannitol were sieved through No. 35 sieve and mixed with each other in a high-speed mixer. Meanwhile, hydroxypropylcellulose and citric acid were dissolved in water to prepare a binder solution, which was then kneaded with the mixture. The kneaded material was granulated through No. 18 sieve using an oscillator, and the granules were dried in a hot-water dryer at 60° C. After completion of the drying process, the granules were sieved through No. 20 sieve. The sieved material was finally mixed with butylated hydroxyanisole in a double cone mixer.

In Example 29, simvastatin immediate release granules having the composition and content shown in Table 6 were prepared according to the same method as described above.

3) Mixing and Filling in Capsule

The compositions, obtained in the step 1) and 2), were mixed with each other in a double cone mixer. The mixture was mixed with starch glycolate sodium in the double cone mixer. Then, the mixture was finally mixed with magnesium stearate. The resulting mixture was placed in a powder feeder and filled in capsules using a capsule filling machine, thus preparing a capsule-type lag time delayed-release formulation.

TABLE 4

| | | Composition ratio (mg/tablet) Examples | | | | | | | | | |
|---|---|---|---|---|---|---|---|---|---|---|---|
| | Components | 1 | 2 | 3 | 4 | 5 | 6 | 7 | 8 | 9 | 10 |
| lag time Delayed-release layer | Losartan potassium | 50.0 | 50.0 | 50.0 | 50.0 | 50.0 | 50.0 | 50.0 | 50.0 | 50.0 | 50.0 |
| | Candesartan | | | | | | | | | | |
| | Telmisartan | | | | | | | | | | |
| | Olmesartan | | | | | | | | | | |
| | Eprosartan | | | | | | | | | | |
| | Microcrystalline cellulose | 14.0 | 14.0 | 14.0 | 14.0 | 14.0 | 14.0 | 14.0 | 14.0 | 14.0 | 14.0 |

TABLE 4-continued

| | | Composition ratio (mg/tablet) Examples | | | | | | | | | |
|---|---|---|---|---|---|---|---|---|---|---|---|
| | Components | 1 | 2 | 3 | 4 | 5 | 6 | 7 | 8 | 9 | 10 |
| | Pregelatinized starch | 10.0 | 10.0 | 10.0 | 10.0 | 10.0 | 10.0 | 10.0 | 10.0 | 10.0 | 10.0 |
| | Copovidone | 4.5 | 4.5 | 4.5 | 4.5 | 4.5 | 4.5 | 4.5 | 4.5 | 4.5 | 4.5 |
| | Aerosil 200 | 1.0 | 1.0 | 1.0 | 1.0 | 1.0 | 1.0 | 1.0 | 1.0 | 1.0 | 1.0 |
| | Crosslinked polyvinylpyrrolidone | | | | | | 4.0 | 8.0 | 12.0 | | |
| | Hydroxypropylcellulose Kollicoat SR30D | | | | | | | | | | |
| | Hydroxypropyl methylcellulose | 0.8 | | | | | | | | 0.8 | 0.8 |
| | Hydroxypropyl methylcellulose phthalate | | | | | | | | | | |
| | Polyethyleneglycol 6000 | | | | | | | | | | |
| | Celluloseacetate (32% acetyl group) | | | | | | | | | | |
| | Celluloseacetate (39.8% acetyl group) | | | | | | | | | | |
| | Ethyl cellulose | | 8.0 | 12.0 | 16.0 | 20.0 | 16.0 | 16.0 | 16.0 | | |
| | Methacrylic acid copolymer type C | 8.0 | 8.0 | 8.0 | 8.0 | 8.0 | 8.0 | 8.0 | 8.0 | 8.0 | 8.0 |
| | Sodium chloride | | | | | | | | | | |
| | Magnesium stearate | 1.5 | 1.5 | 1.5 | 1.5 | 1.5 | 1.5 | 1.5 | 1.5 | 1.5 | 1.5 |
| Immediate release layer | Simvastatin | 20.0 | 20.0 | 20.0 | 20.0 | 20.0 | 20.0 | 20.0 | 20.0 | | |
| | Lovastatin | | | | | | | | | 20.0 | |
| | Atorvastatin | | | | | | | | | | 20.0 |
| | Microcrystalline cellulose | 95.0 | 95.0 | 95.0 | 95.0 | 95.0 | 95.0 | 95.0 | 95.0 | 95.0 | 95.0 |
| | D-mannitol | | | | | | | | | | |
| | Lactose | 268.0 | 268.0 | 268.0 | 268.0 | 268.0 | 268.0 | 268.0 | 268.0 | 268.0 | 268 |
| | Corn starch | 50.0 | 50.0 | 50.0 | 50.0 | 50.0 | 50.0 | 50.0 | 50.0 | 50.0 | 50.0 |
| | Starch glycolate sodium | 15.0 | 15.0 | 15.0 | 15.0 | 15.0 | 15.0 | 15.0 | 15.0 | 15.0 | 15.0 |
| | Butylated hydroxyanisole | 0.35 | 0.35 | 0.35 | 0.35 | 0.35 | 0.35 | 0.35 | 0.35 | 0.35 | 0.35 |
| | Hydroxypropyl cellulose | 10.0 | 10.0 | 10.0 | 10.0 | 10.0 | 10.0 | 10.0 | 10.0 | 10.0 | 10.0 |
| | Citric acid | 6.5 | 6.5 | 6.5 | 6.5 | 6.5 | 6.5 | 6.5 | 6.5 | 6.5 | 6.5 |
| | Magnesium stearate | 5.05 | 5.05 | 5.05 | 5.05 | 5.05 | 5.05 | 5.05 | 5.05 | 5.05 | 5.05 |
| Coating layer | Hydroxypropyl methylcellulose 2910 | 15.8 | 15.8 | 15.8 | 15.8 | 15.8 | 15.8 | 15.8 | 15.8 | 15.8 | 15.8 |
| | Hydroxyppropyl cellulose | | | | | | | | | | |
| | Titanium oxide | 2.3 | 2.3 | 2.3 | 2.3 | 2.3 | 2.3 | 2.3 | 2.3 | 2.3 | 2.3 |
| | Talc | 1.5 | 1.5 | 1.5 | 1.5 | 1.5 | 1.5 | 1.5 | 1.5 | 1.5 | 1.5 |
| | Total | 579.3 | 586.5 | 590.5 | 594.5 | 598.5 | 598.5 | 602.5 | 606.5 | 579.3 | 579.3 |

TABLE 5

| | | Composition ratio (mg/tablet) Examples | | | | | | | | | |
|---|---|---|---|---|---|---|---|---|---|---|---|
| | Components | 11 | 12 | 13 | 14 | 15 | 16 | 17 | 18 | 19 | 20 |
| lag time Delayed- release layer | Losartan potassium | | | | | 50.0 | 50.0 | 50.0 | 50.0 | 50.0 | 100.0 |
| | Candesartan | 16.0 | | | | | | | | | |
| | Telmisartan | | 40.0 | | | | | | | | |
| | Olmesartan | | | 20.0 | | | | | | | |
| | Eprosartan | | | | 600.0 | | | | | | |
| | Microcrystalline cellulose | 14.0 | 14.0 | 14.0 | 60.0 | 25.0 | 137.0 | 123.0 | 25.0 | 137.0 | 123.0 |
| | Pregelatinized starch | 10.0 | 10.0 | 10.0 | 40.0 | | | | | | |
| | Copovidone | 4.5 | 4.5 | 4.5 | 18.0 | | | | | | |
| | Aerosil 200 | 1.0 | 1.0 | 1.0 | 4.0 | | | | | | |
| | Crosslinked polyvinylpyrrolidone | | | | | 50.0 | | | 50.0 | | |
| | Hydroxypropylcellulose | | | | | 5.0 | | | 5.0 | | |
| | Kollicoat SR30D | | | | | | | 24.0 | | | 48.0 |

TABLE 5-continued

| | | Composition ratio (mg/tablet) Examples | | | | | | | | | |
|---|---|---|---|---|---|---|---|---|---|---|---|
| | Components | 11 | 12 | 13 | 14 | 15 | 16 | 17 | 18 | 19 | 20 |
| | Hydroxypropyl methylcellulose | 0.5 | 0.7 | 0.5 | 2.0 | 2.0 | 4.0 | | 2.0 | 4.0 | |
| | Hydroxypropyl methylcellulose phthalate | | | | | | 6.0 | | | 6.0 | |
| | Polyethyleneglycol 6000 | | | | | | | | | | |
| | Celluloseacetate (32% acetyl group) | | | | | 20.0 | | | 20.0 | | |
| | Celluloseacetate (39.8% acetyl group) | | | | | 20.0 | | | 20.0 | | |
| | Methacrylic acid copolymer type C | 4.7 | 7.1 | 5.1 | 20.0 | | | | | | |
| | Sodium chloride | | | | | 25.0 | | | 25.0 | | |
| | Magnesium stearate | 1.5 | 1.5 | 1.5 | 6.0 | | | 20.0 | 3.0 | 3.0 | 3.0 |
| Immediate release layer | Simvastatin | 20.0 | 20.0 | 20.0 | 20.0 | 20.0 | 20.0 | 20.0 | 20.0 | 20.0 | 20.0 |
| | Lovastatin | | | | | | | | | | |
| | Atorvastatin | | | | | | | | | | |
| | Microcrystalline cellulose | 95.0 | 95.0 | 95.0 | 57.0 | 95.0 | 95.0 | 57.0 | 57.0 | 57.0 | 57.0 |
| | D-maninitol | | | | 112.5 | | | 112.5 | 112.5 | 112.5 | 112.5 |
| | Lactose | 268.0 | 268.0 | 268.0 | | 268.0 | 268.0 | | | | |
| | Corn starch | 50.0 | 50.0 | 50.0 | | 50.0 | 50.0 | | | | |
| | Starch glycolate sodium | 15.0 | 15.0 | 15.0 | 2.0 | 15.0 | 15.0 | 2.0 | 2.0 | 2.0 | 2.0 |
| | Butylated hydroxyanisole | 0.35 | 0.35 | 0.35 | 0.1 | 0.35 | 0.35 | 0.1 | 0.1 | 0.1 | 0.1 |
| | Hydroxypropyl cellulose | 10.0 | 10.0 | 10.0 | 5.0 | 10.0 | 10.0 | 5.0 | 5.0 | 5.0 | 5.0 |
| | Citric acid | 6.5 | 6.5 | 6.5 | 2 | 6.5 | 6.5 | 2.0 | 2.0 | 2.0 | 2.0 |
| | Magnesium stearate | 5.05 | 5.05 | 5.05 | 4.5 | 5.05 | 5.05 | 4.5 | 1.5 | 1.5 | 1.5 |
| Coating layer | Hydroxypropyl methylcellulose 2910 | 18.3 | 19.2 | 18.4 | 33.4 | 2.6 | 2.6 | 2.6 | 2.6 | 2.6 | 2.6 |
| | Hydroxyppropyl cellulose | | | | | 2.6 | 2.6 | 2.6 | 2.6 | 2.6 | 2.6 |
| | Titanium oxide | 2.7 | 2.9 | 2.8 | 5.1 | 2.3 | 2.3 | 2.3 | 2.3 | 2.3 | 2.3 |
| | Talc | 1.9 | 1.9 | 1.8 | 3.3 | 1.5 | 1.5 | 1.5 | 1.5 | 1.5 | 1.5 |
| | Total | 545.0 | 572.7 | 549.5 | 994.9 | 409.1 | 409.1 | 409.1 | 409.1 | 409.1 | 483.0 |

TABLE 6

| | | Composition ratio (mg/tablet) Examples | | | | | | | | |
|---|---|---|---|---|---|---|---|---|---|---|
| | Components | 21 | 22 | 23 | 24 | 25 | 26 | 27 | 28 | 29 |
| lag time Delayed-release layer | Losartan potassium | | | | 50.0 | 50.0 | 50.0 | 50.0 | 50.0 | 50.0 |
| | Valsartan | 80.0 | 80.0 | | | | | | | |
| | Irbesartan | | | 150.0 | | | | | | |
| | Microcrystalline cellulose | 40.0 | 219.2 | 75.0 | 25.0 | 137.0 | 25.0 | 137.0 | 25.0 | 137.0 |
| | Pregelatinized starch | | | | | | | | | |
| | Copovidone | | | | | | | | | |
| | Aerosil 200 | | | | | | | | | |
| | Crosslinked polyvinylpyrrolidone | 80.0 | | 150.0 | 50.0 | | 50.0 | | 50.0 | |
| | Hydroxypropylcellulose | 8.0 | | 15.0 | 5.0 | | 5.0 | | 5.0 | |
| | Kollicoat SR30D | | | | | | | | | |
| | Hydroxypropyl methylcellulose | 3.2 | 6.4 | 6.0 | 2.0 | 4.0 | 2.0 | 4.0 | 2.0 | 4.0 |
| | Hydroxypropyl methylcellulose phthalate | | 9.6 | | | 6.0 | | 6.0 | | 6.0 |
| | Polyethyleneglycol 6000 | | | | | | | | | |
| | Celluloseacetate (32% acetyl group) | 32.0 | | 60.0 | 20.0 | | 20.0 | | 20.0 | |
| | Celluloseacetate (39.8% acetyl group) | 32.0 | | 60.0 | 20.0 | | 20.0 | | 20.0 | |
| | Methacrylic acid copolymer type C | | | | | | | | | |
| | Sodium chloride | 40.0 | | 75.0 | 25.0 | | 25.0 | | 25.0 | |
| | Magnesium stearate | 4.8 | 4.8 | 9.0 | 3.0 | 3.0 | 3.0 | 3.0 | | |

TABLE 6-continued

| | | Composition ratio (mg/tablet) Examples | | | | | | | | |
|---|---|---|---|---|---|---|---|---|---|---|
| | Components | 21 | 22 | 23 | 24 | 25 | 26 | 27 | 28 | 29 |
| Immediate release layer | Simvastatin | 20.0 | 20.0 | 20.0 | | | | | 20.0 | 20.0 |
| | Lovastatin | | | | 20.0 | 20.0 | | | | |
| | Atorvastatin | | | | | | 20.0 | 20.0 | | |
| | Microcrystalline cellulose | 57.0 | 57.0 | 57.0 | 57.0 | 57.0 | 57.0 | 57.0 | 57.0 | 57.0 |
| | D-mannitol | 112.5 | 112.5 | 112.5 | 112.5 | 112.5 | 112.5 | 112.5 | 112.5 | 112.5 |
| | Lactose | | | | | | | | | |
| | Corn starch | | | | | | | | | |
| | Starch glycolate sodium | 2.0 | 2.0 | 2.0 | 2.0 | 2.0 | 2.0 | 2.0 | 2.0 | 2.0 |
| | Butylated hydroxyanisole | 0.1 | 0.1 | 0.1 | 0.1 | 0.1 | 0.1 | 0.1 | 0.1 | 0.1 |
| | Hydroxypropyl cellulose | 5.0 | 5.0 | 5.0 | 5.0 | 5.0 | 5.0 | 5.0 | 5.0 | 5.0 |
| | Citric acid | 2.0 | 2.0 | 2.0 | 2.0 | 2.0 | 2.0 | 2.0 | 2.0 | 2.0 |
| | Magnesium stearate | 1.5 | 1.5 | 4.5 | 1.5 | 1.5 | 1.5 | 1.5 | 4.5 | 4.5 |
| Coating layer | Hydroxypropyl methylcellulose 2910 | 2.6 | 2.6 | 2.6 | 2.6 | 2.6 | 2.6 | 2.6 | | |
| | Hydroxyppropyl cellulose | 2.6 | 2.6 | 2.6 | 2.6 | 2.6 | 2.6 | 2.6 | | |
| | Titanium oxide | 2.3 | 2.3 | 2.3 | 2.3 | 2.3 | 2.3 | 2.3 | | |
| | Talc | 1.5 | 1.5 | 1.5 | 1.5 | 1.5 | 1.5 | 1.5 | | |
| | Total | 529.1 | 529.1 | 809.1 | 409.1 | 409.1 | 409.1 | 409.1 | 400.1 | 400.1 |

Test Example 1

Comparative Dissolution Profile Test

Comparative dissolution profile tests of the losartan/simvastatin two-phase combination lag time delayed-release tablet, prepared in Example 1, and control drugs (Zocor® (simvastatin single tablet); Cozaar® (losartan single tablet)), were performed. The dissolution profile test of the simvastatin component was performed based on the United States Pharmacopoeia (USP30), and the dissolution profile test of the losartan component was performed for a total of 480 minutes, in which the dissolution medium was changed from artificial gastric juice to artificial intestinal juice starting from 120 minutes after the start of the test. The dissolution profile test of each component was performed in the following manner, and the test results are shown in FIG. 1.

As can be seen in FIG. 1, when the dissolution profile test was performed in the following conditions, the simvastatin component of the two-phase combination tablet of the present invention showed a dissolution profile substantially equal to that of control drug Zocor®, but the losartan component showed a very slow dissolution rate compared to that of control drug Cozaar®. In the dissolution profile test results for the losartan component, the dissolution rate of the losartan component up to 120 minutes corresponding to the artificial gastric juice zone was less than 10% in the losartan/simvastatin two-phase combination lag time delayed-release tablet of the present invention, but was about 60% in the control formulation. The dissolution rate of the losartan component in the subsequent artificial intestinal juice zone was 100% up to a total of 150 minutes in the control formulation, but was about 20% up to a total of 240 minutes in the losartan/simvastatin two-phase combination lag time delayed-release tablet of the present invention, suggesting that dissolution rate of the losartan component in the inventive controlled-release tablet was much slower than that in the control formulation.

As described above, the early release of losartan in the losartan/simvastatin two-phase combination lag time delayed-release tablet of the present invention is much slower than simvastatin, unlike dissolution profiles obtained when the losartan single tablet and the simvastatin single tablet, as the control drugs, are administered simultaneously. Thus, in the case of the inventive tablet, the time for metabolism-related enzyme cytochrome P450 to be regenerated after simvastatin is metabolized first in the liver can be sufficiently ensured.

[Simvastatin Test Method]

Dissolution profile test: performed based on the paragraph "simvastatin tablet" in the United States Pharmacopoeia (USP30).

Test method: paddle method, 50 rpm.

Dissolution medium: 900 ml of pH=7.0 buffer (composition=0.01M sodium dihydrogen phosphate solution containing 0.5 wt % of sodium lauryl sulfate as surfactant).

Analysis method: UV/Vis spectrophotometry (detection wavelength=247-257 nm).

[Losartan Potassium Test Method]

Dissolution profile test: performed based on dissolution test method of general test methods in the Korean Pharmacopoeia, eighth edition.

Test method: paddle method, 50 rpm.

Dissolution media: 750 ml of 0.01M hydrochloric acid solution (artificial gastric juice); 1000 ml of pH 6.8 phosphate buffer solution (artificial intestinal juice).

Analysis method: UV/Vis spectrophotometry (detection wavelength=below 230 nm).

Test Example 2

Comparative Dissolution Profile Test

Figure 2:
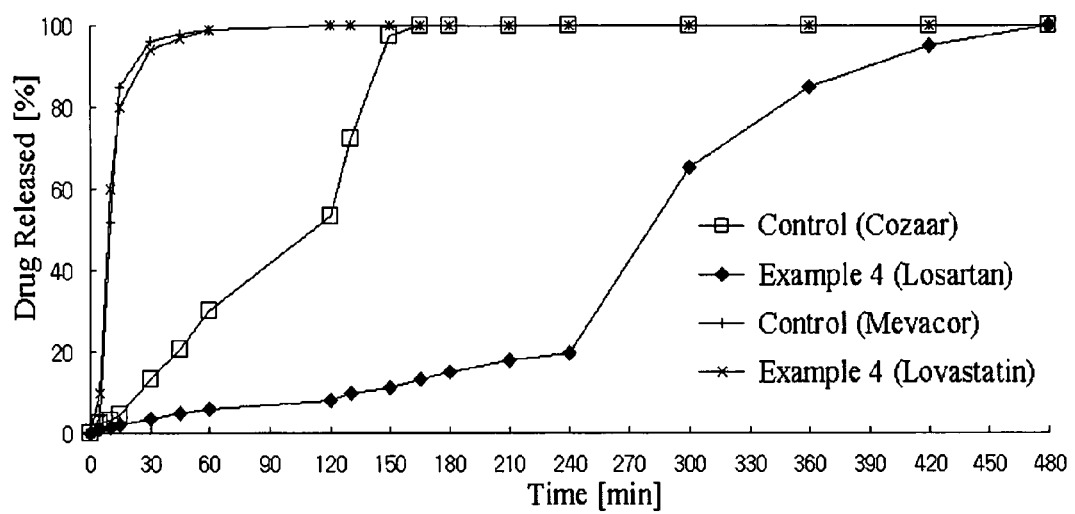
FIG. 2 is a diagram showing the comparative dissolution profiles of a lag time delayed-release formulation of losartan/lovastatin, prepared in Example 9, and the losartan and lovastatin components of single drugs, Cozaar® and Mevacor®, as control groups.

Comparative dissolution profile tests of the losartan/lovastatin two-phase combination lag time delayed-release tablet, prepared in Example 9, and control drugs (Mevacor® (lovastatin single tablet); Cozaar® (losartan single tablet)), were performed. The dissolution profile test of the lovastatin component was performed based on the United States Pharmacopoeia (USP30), and the dissolution profile test of the losartan component was performed up to a total of 480 minutes, in which the dissolution medium was changed from artificial gastric juice to artificial intestinal juice starting from 120 minutes after the start of the test. The dissolution profile test of each component was performed in the following manner, and the test results are shown in FIG. 2. The analysis of the losartan component was performed in the same manner as in Example 1.

As can be seen in FIG. 2, when the dissolution profile test was performed in the following conditions, the lovastatin component of the two-phase combination tablet of the present invention showed a dissolution profile substantially equal to that of the control drug Mevacor®, but the losartan component showed a very slow dissolution rate compared to that of the control drug Cozaar®. In the dissolution profile test results for the losartan component, the dissolution rate of the losartan component up to 120 minutes corresponding to the artificial gastric juice zone was less than 10% in the losartan/lovastatin two-phase combination lag time delayed-release tablet of the present invention, but was about 60% in the control drug. The dissolution rate of the losartan component in the subsequent artificial intestinal juice zone was 100% up to a total of 150 minutes in the control formulations, but was about 20% up to a total of 240 minutes in the losartan/lovastatin two-phase combination lag time delayed-release tablet of the present invention, suggesting that dissolution rate of the losartan component in the inventive controlled-release tablet was much slower than that in the control drug.

As described above, the early release of losartan in the losartan/lovastatin two-phase combination lag time delayed-release tablet of the present invention is much slower than simvastatin, unlike dissolution profiles obtained when the losartan single tablet and the lovastatin single tablet, as the control drugs, are administered simultaneously. Thus, in the case of the inventive tablet, the time for metabolism-related enzyme cytochrome P450 to be regenerated after lovastatin is metabolized first in the liver can be sufficiently ensured.

[Lovastatin Test Method]

Dissolution profile test: performed based on the paragraph "lovastatin tablet" in the United States Pharmacopoeia (USP30).

Test method: paddle method, 50 rpm.

Dissolution medium: 900 ml of pH=7.0 buffer (composition=0.01M sodium dihydrogen phosphate solution containing 2 wt % of sodium lauryl sulfate as surfactant).

Analysis method: high-performance liquid chromatography.

Detection wavelength: 230 nm.

Mobile phase: acetonitrile: 0.02M sodium dihydrogen phosphate buffer (pH=4.0): methanol=5:3:1.

Column stainless column (having an inner diameter of 4.6 cm and a length of 250 mm) packed with octadecyl silyl silica gel.

Flow rate: 1.5 mL/min.

Test Example 3

Comparative Dissolution Profile Test

Comparative dissolution profile tests of the formulations prepared in Examples 2-5 were performed. The dissolution profile test of each component was performed in the same manner as in Test Example 1, and the test results are shown in FIG. 3.

Figure 3:
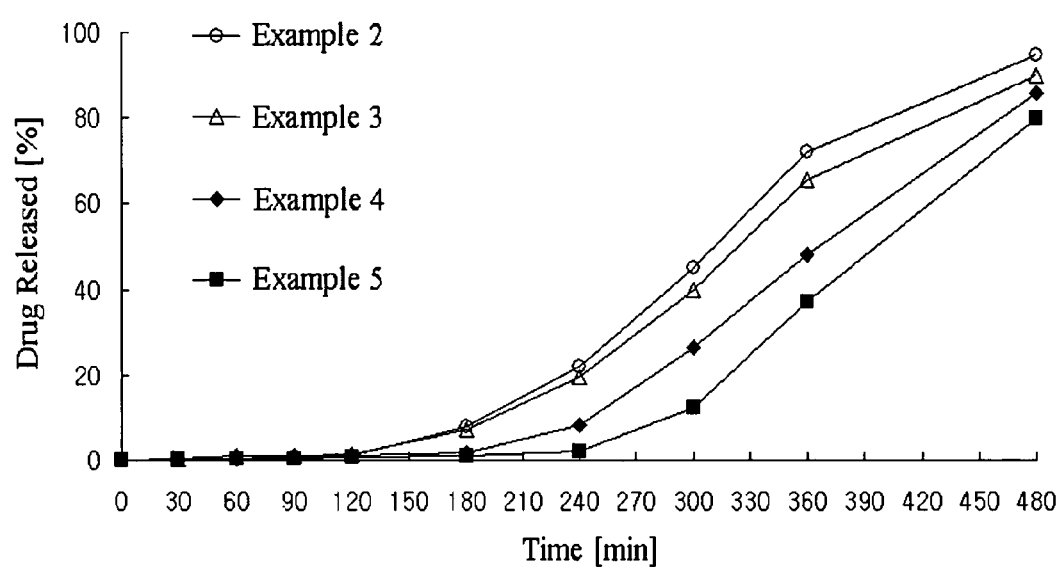
FIG. 3 is a graphic diagram showing the dissolution profiles of Example from 2 to 5.

As can be seen in FIG. 3, when the dissolution profile test was performed in the conditions of Test Example 1, the losartan component of the dry-coated tablet of the present invention showed a decrease in dissolution rate with an increase in the amount of ethylcellulose used. The formulations of Examples 2-5, coated with ethylcellulose, showed a losartan dissolution rate of less than 20% up to a total of 240 minutes.

As described above, the early release of losartan in the inventive dry-coated tablet of losartan/simvasatin can be delayed up to the intended time by controlling the amount of ethylcellulose coated.

As described above, the early release of losartan in the losartan/simvastatin two-phase combination lag time delayed-release tablet of the present invention is much slower than simvastatin, unlike dissolution profiles obtained when the losartan single tablet and the simvastatin single tablet, as the control drugs, are administered simultaneously. Thus, in the case of the inventive tablet, the time for metabolism-related enzyme cytochrome P450 to be regenerated after simvastatin is metabolized first in the liver can be sufficiently ensured.

Test Example 4

Comparative Dissolution Profile Test

Figure 4:
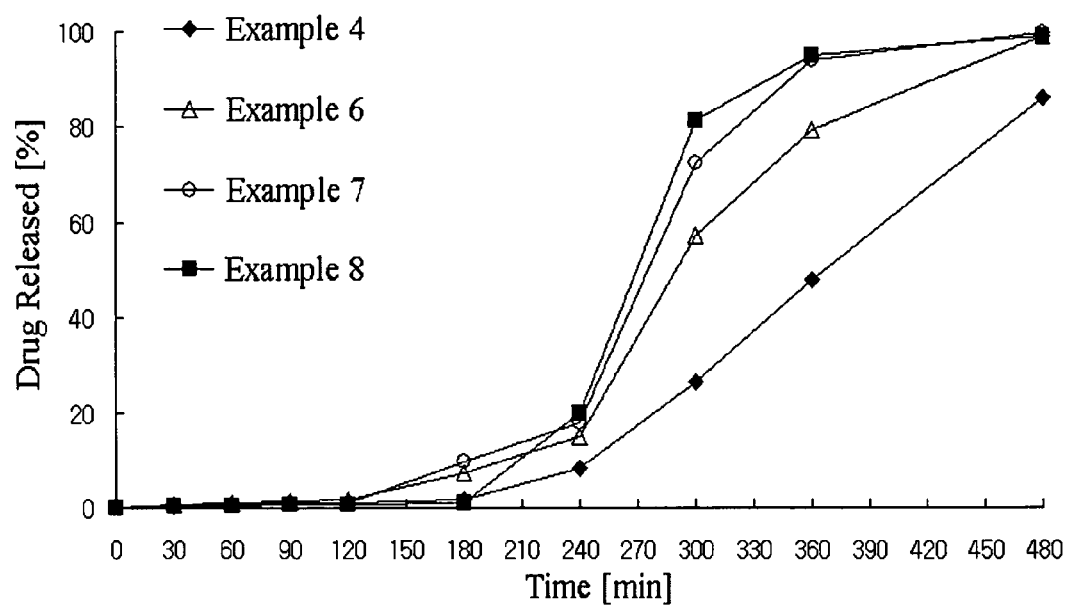
FIG. 4 is a graphic diagram showing the dissolution profiles of Example 4 and from 6 to 8.

Comparative dissolution profile tests of the formulations prepared in Examples 4 and 6-8 were performed. The dissolution profile test of each component was performed in the same manner as in Test Example 1, and the test results are shown in FIG. 4.

As can be seen in Table 4, in the results of the dissolution profile test performed in the conditions of Test Example 1, the losartan component of the dry-coated tablet of the present invention was rapidly released after an intended delay time, when the delayed-release layer coated with ethyl cellulose contained crosslinked polyvinylpyrrolidone. The dissolution rate of the losartan component was less than 20% up to a total of 240 minutes, and the losartan component was rapidly released with an increase in the amount of crosslinked polyvinylpyrrolidone used.

As described above, the losartan component of the inventive dry-coated tablet of losartan/simvasatin can be rapidly released after an intended delay time by controlling the amount of crosslinked polyvinylpyrrolidone used in the delayed-release layer.

As described above, the early release of losartan in the losartan/simvastatin two-phase combination lag time delayed-release tablet of the present invention is much slower than simvastatin, unlike dissolution profiles obtained when the losartan single tablet and the simvastatin single tablet, as the control drugs, are administered simultaneously. Thus, in the case of the inventive tablet, the time for metabolism-related enzyme cytochrome P450 to be regenerated after simvastatin is metabolized first in the liver can be sufficiently ensured.

Test Example 5

Comparative Dissolution Profile Test

Figure 5:
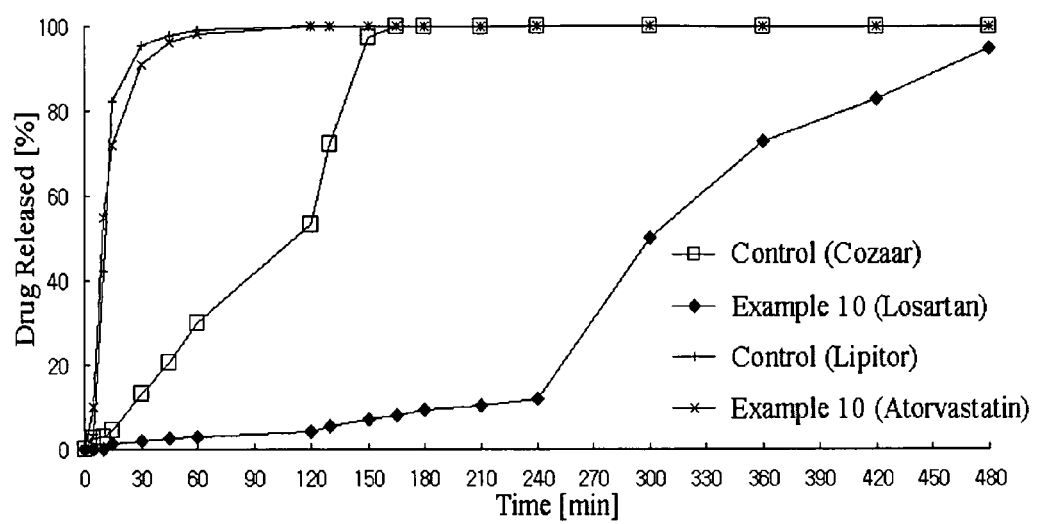
FIG. 5 is a diagram showing the comparative dissolution profiles of a lag time delayed-release formulation of losartan/atorvastatin, prepared in Example 10, and the losartan and atorvastatin components of single drugs, Cozaar® and Lipitor®, as control groups.

Comparative dissolution profile tests of the losartan/atorvastatin two-phase combination lag time delayed-release tablet, prepared in Example 10, and control drugs (Lipitor® (atorvastatin single tablet); Cozaar® (losartan single tablet), were performed. The dissolution profile test of atorvastatin was performed based on the dissolution test method of general test methods contained in the Korean Pharmacopoeia, eighth edition, and the dissolution profile test of the losartan component was performed for a total of 480 minutes, in which the dissolution medium was changed from artificial gastric juice to artificial intestinal juice starting from 120 minutes after the start of the test. The dissolution profile test of each component was performed in the following manner, and the test results are shown in FIG. 5. The analysis of the losartan component was performed in the same manner as in Example 1.

As can be seen in FIG. 5, when the dissolution profile test was performed in the following conditions, the atorvastatin component of the two-phase combination tablet of the present invention showed a dissolution profile substantially equal to that of the control drug Lipitor®, but the losartan component showed a very slow dissolution rate compared to that of the control drug Cozaar®. In the dissolution profile test results for the losartan component, the dissolution rate of the losartan component up to 120 minutes corresponding to the artificial gastric juice zone was less than 10% in the losartan/atorvastatin two-phase combination lag time delayed-release tablet of the present invention, but was about 60% in the control drug. The dissolution rate of the losartan component in the subsequent artificial intestinal juice zone was 100% up to a total of 150 minutes in the control formulations, but was about 20% up to a total of 240 minutes in the losartan/atorvastatin two-phase combination lag time delayed-release tablet of the present invention, suggesting that dissolution rate of the losartan component in the inventive combination lag time delayed-release tablet was much slower than that in the control drug.

As described above, the early release of losartan in the losartan/atorastatin two-phase combination lag time delayed-release tablet of the present invention is much slower than simvastatin, unlike dissolution profiles obtained when the losartan single tablet and the atorvastatin single tablet, as the control drugs, are administered simultaneously. Thus, in the case of the inventive tablet, the time for metabolism-related enzyme cytochrome P450 to be regenerated after atorvastatin is metabolized first in the liver can be sufficiently ensured.

[Atorvastatin Test Method]

Dissolution profile test: performed based on dissolution test method of general test methods in the Korean Pharmacopoeia, eighth edition.

Test method: paddle method, 50 rpm.

Dissolution medium: 900 ml of pH=7.0 buffer (composition=0.01M sodium dihydrogen phosphate solution containing 2 wt % of sodium lauryl sulfate as surfactant).

Analysis method: high-performance liquid chromatography.

Detection wavelength: 247 nm

Mobile phase: 0.02M sodium dihydrogen phosphate buffer (pH=4.0):methanol=67:33.

Column: Stainless column (having an inner diameter of 4.6 cm and a length of 250 mm) packed with octadecyl silyl silica gel.

Flow rate: 1.5 mL/min.

Test Example 6

Comparative Dissolution Profile Test

Comparative dissolution profile tests of the losartan/simvastatin two-phase combination lag time delayed-release tablets, prepared in Examples 14 and 19, and control drugs (Zocor® (simvastatin single tablet); Cozaar® (losartan single tablet)), were performed. The dissolution profile test of the simvastatin component was performed based on the United States Pharmacopoeia (USP30), and the dissolution profile test of the losartan component was performed for a total of 480 minutes, in which the dissolution medium was changed from artificial gastric juice to artificial intestinal juice starting from 120 minutes after the start of the test. The dissolution profile test of each component was performed in the same manner as in Test Example 1, and the test results are shown in FIG. 6.

Figure 6:
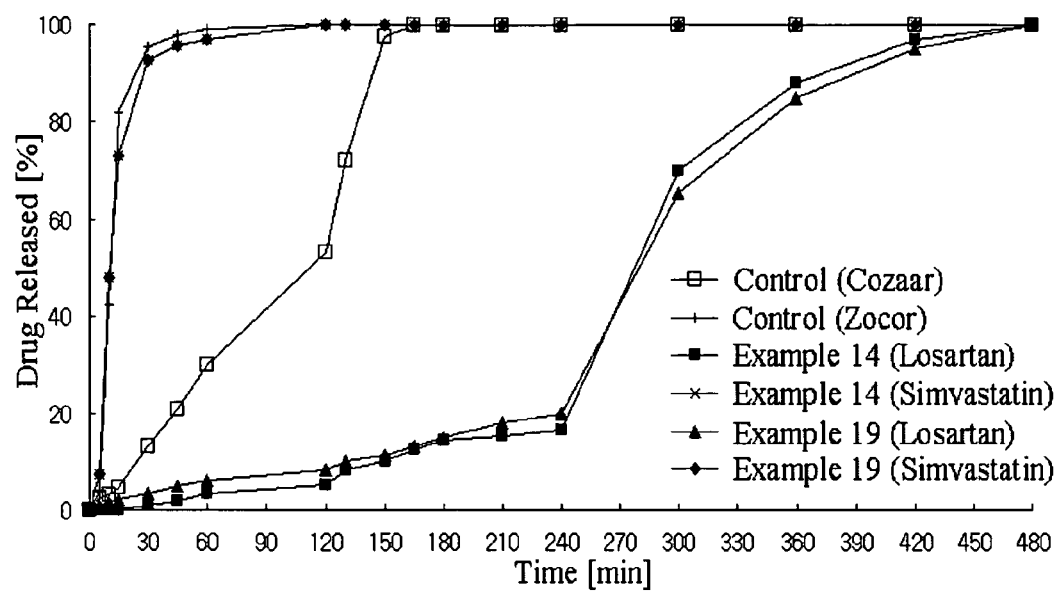
FIG. 6 is a diagram showing the comparative dissolution profiles of a lag time delayed-release formulation of losartan/simvastatin, prepared in each of Examples 14 and 19, and the losartan and simvastatin components of single drugs, Cozaar® and Zocor®, as control groups.

As can be seen in FIG. 6, when the dissolution profile test was performed in the conditions of Test Example 1, the simvastatin component of the two-phase combination tablet of the present invention showed a dissolution profile substantially equal to that of the control drug Zocor®, but the losartan component showed a very slow dissolution rate compared to that of the control drug Cozaar®. In the dissolution profile test results for the losartan component, the dissolution rate of the losartan component up to 120 minutes corresponding to the artificial gastric juice zone was less than 10% in the losartan/simvastatin two-phase combination lag time delayed-release tablets of the present invention, but was about 60% in the control formulation. The dissolution rate of the losartan component in the subsequent artificial intestinal juice zone was 100% up to a total of 150 minutes in the control formulation, but was about 20% up to a total of 240 minutes in the losartan/simvastatin two-phase combination lag time delayed-release tablet of the present invention, suggesting that dissolution rate of the losartan component in the inventive lag time delayed-release tablet was much slower than that in the control formulation.

As described above, the early release of losartan in the losartan/simvastatin two-phase combination lag time delayed-release tablet of the present invention is much slower than simvastatin, unlike dissolution profiles obtained when the losartan single tablet and the simvastatin single tablet, as the control drugs, are administered simultaneously. Thus, in the case of the inventive tablet, the time for metabolism-related enzyme cytochrome P450 to be regenerated after simvastatin is metabolized first in the liver can be sufficiently ensured.

Test Example 7

Comparative Dissolution Profile Test

Figure 7:
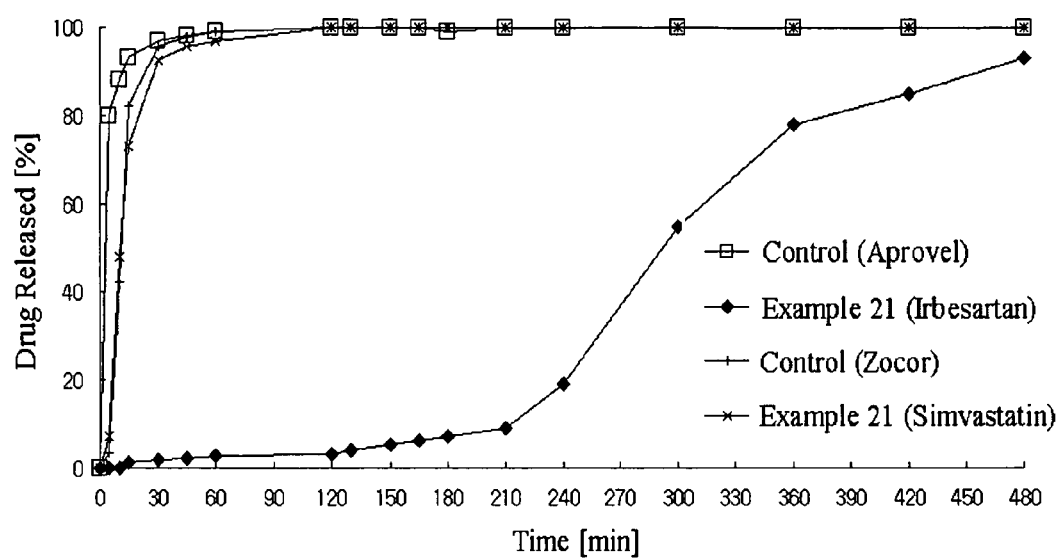
FIG. 7 is a diagram showing the comparative dissolution profiles of a lag time delayed-release formulation of irbesartan/simvastatin, prepared in each of Example 21, and the irbesartan and simvastatin components of single drugs, Aprovel® and Zocor®, as control groups.

Comparative dissolution profile tests of the Irbesartan/simvastatin two-phase combination lag time delayed-release tablet, prepared in Example 21, and control drugs (Zocor® (simvastatin single tablet); Aprovel® (Irbesartan single tablet)), were performed. The dissolution profile test of the simvastatin component was performed based on the United States Pharmacopoeia (USP30), and the dissolution profile test of the irbesartan component was performed for a total of 480 minutes, in which the dissolution medium was changed from artificial gastric juice to artificial intestinal juice starting from 120 minutes after the start of the test. The dissolution profile test of each component was performed in the following manner, and the test results are shown in FIG. 7. The analysis of the simvastatin component was performed in the same manner as in Test Example 1.

As can be seen in FIG. 7, when the dissolution profile test was performed in the following conditions, the simvastatin component of the two-phase combination tablet of the present invention showed a dissolution profile substantially equal to that of the control drug Zocor®, but the irbesartan component showed a very slow dissolution rate compared to that of the control drug Aprovel®. In the dissolution profile test results for the irbesartan component, the dissolution rate of the irbesartan component up to 120 minutes corresponding to the artificial gastric juice zone was less than 10% in the irbesartan/simvastatin two-phase combination lag time delayed-release tablet of the present invention, but was about 100% in the control formulation. The dissolution rate of the irbesartan component in the subsequent artificial intestinal juice zone was 100% up to a total of 150 minutes in the control formulation, but was about 20% up to a total of 240 minutes in the irbesartan/simvastatin two-phase combination lag time delayed-release tablet of the present invention, suggesting that dissolution rate of the irbesartan component in the inventive lag time delayed-release tablet was much slower than that in the control formulation.

As described above, the early release of irbesartan in the irbesartan/simvastatin two-phase combination lag time delayed-release tablet of the present invention is much slower than simvastatin, unlike dissolution profiles obtained when the irbesartan single tablet and the simvastatin single tablet, as the control drugs, are administered simultaneously. Thus, in the case of the inventive tablet, the time for metabolism-related enzyme cytochrome P450 to be regenerated after simvastatin is metabolized first in the liver can be sufficiently ensured.

[Irbesartan Test Method]
Dissolution test: performed based on dissolution test method of general test methods in the Korean Pharmacopoeia, eighth edition.
Test method: paddle method, 50 rpm.
Dissolution media: 750 ml of 0.01M hydrochloric acid solution (artificial gastric juice); 1000 ml of pH 6.8 phosphate buffer solution (artificial intestinal juice).
Analysis method: high-performance liquid chromatography.
Detection wavelength: 220 nm.
Mobile phase: acetonitrile: phosphate buffer (pH=3.7)=33:67.
Column stainless column (having an inner diameter of 4.0 cm and a length of 250 mm) packed with octadecyl silyl silica gel.
Flow rate: 1.0 mL/min.

Test Example 8

Animal Study

In this Test Example, an animal study was performed as described in Table 7 below in order to confirm the effect of the inventive composition. Specifically, in a control group, commercially available control drugs (Zocor® tablet, MSD (simvastatin single tablet) and Cozaar® tablet, MSD (losartan single tablet)) were simultaneously administered. In a test group, the drugs were administered at different times, such that the release times of the drugs were the same as in the composition provided in Example of the present invention, and thus the effects of the drugs were the same as those of the inventive composition.

Also, this animal study was designed such that the administration time showing the maximum antihypertensive effect could be confirmed.

TABLE 7

| | | | | |
|---|---|---|---|---|
| Title | Animal study for the comparison of antihypertensive effect between the simultaneous administration of losartan and simvastatin and the administration of the drugs at different times in spontaneously hypertensive rats (SHR) rats. | | | |
| Object | To comparatively evaluate steady-state pharmacokinetic properties, antihypertensive effect and safety between simultaneous administration of losartan and simvastatin and the administration of the drugs at different times and to comparatively evaluate pharmacokinetic properties, antihypertensive effect and safety between administration times. | | | |
| Test subjects | Twenty-five 8-week-old male SHR rats grouped into five groups, each consisting of five animals, and four 9-week-old male Wistar Kyoto rats. | | | |
| Test design | The design of this test is as follows.<br>As test dugs, losartan and simvastatin were used. A total of 29 animals were grouped into the following six groups, each consisting of 5 animals: a saline-administered WKY rat group as a control group; a saline-administered SHR rat group as a screening group; a test group administered with losartan and simvastatin simultaneously in the morning (SM group) (dark conditions); a test group administered with losartan and simvastatin simultaneously in the evening (SN group) (light conditions); a test group administered with losartan and simvastatin at different times in the morning (DM group) (dark conditions); a test group administered with losartan and simvastatin at different times in the evening (DN group) (light conditions) (three big groups: a control group, a screening group and a test group). The drugs were administered for 5 days once a day.<br>Because this study is an animal study using rats as test models, the test was performed in light conditions and dark conditions. The administration time applied in the animal study is conversely applied to humans, because the biorhythm of rats is opposite to the biorhythm of humans. | | | |
| Evaluation method | Evaluation of effects<br>Comparison of changes in systolic blood pressure, diastolic blood pressure, mean blood pressure and pulse rate, measured with automatic blood pressure meter, between the groups administered with the drugs simultaneously in the morning and in evening, and the groups administered with the drugs at different times in the morning and in evening. | | | |
| | | Group name | Administered drugs and method (administrated on concentration of 5 ml/kg) | Animal number |
| Test groups | | Normal (WKY rats, saline) | Administered with saline hourly | 4 |
| | | Vehicle (saline) | Administered with saline hourly | 5 |
| | | Administered with losartan and simvastatin simultaneously in the morning (SM group) (dark conditions) | Administered with losartan and simvastatin simultaneously at 9:30 a.m. | 5 |
| | | Administered with losartan and simvastatin simultaneously in the evening (SN group) (light conditions) | Administered with losartan and simvastatin simultaneously at 7 p.m. | 5 |

TABLE 7-continued

| | | |
|---|---|---|
| Administered with losartan and simvastatin at different times in the morning (DM group) (dark conditions) | Administered with losartan at 9:30 a.m.; Administered with simvastatin at 1:30 p.m. | 5 |
| Administered with losartan and simvastatin at different times in the evening (DN group) (light conditions) | Administered with losartan at 7 p.m.; Administered with simvastatin at 11 p.m. | 5 |

Figure 8:
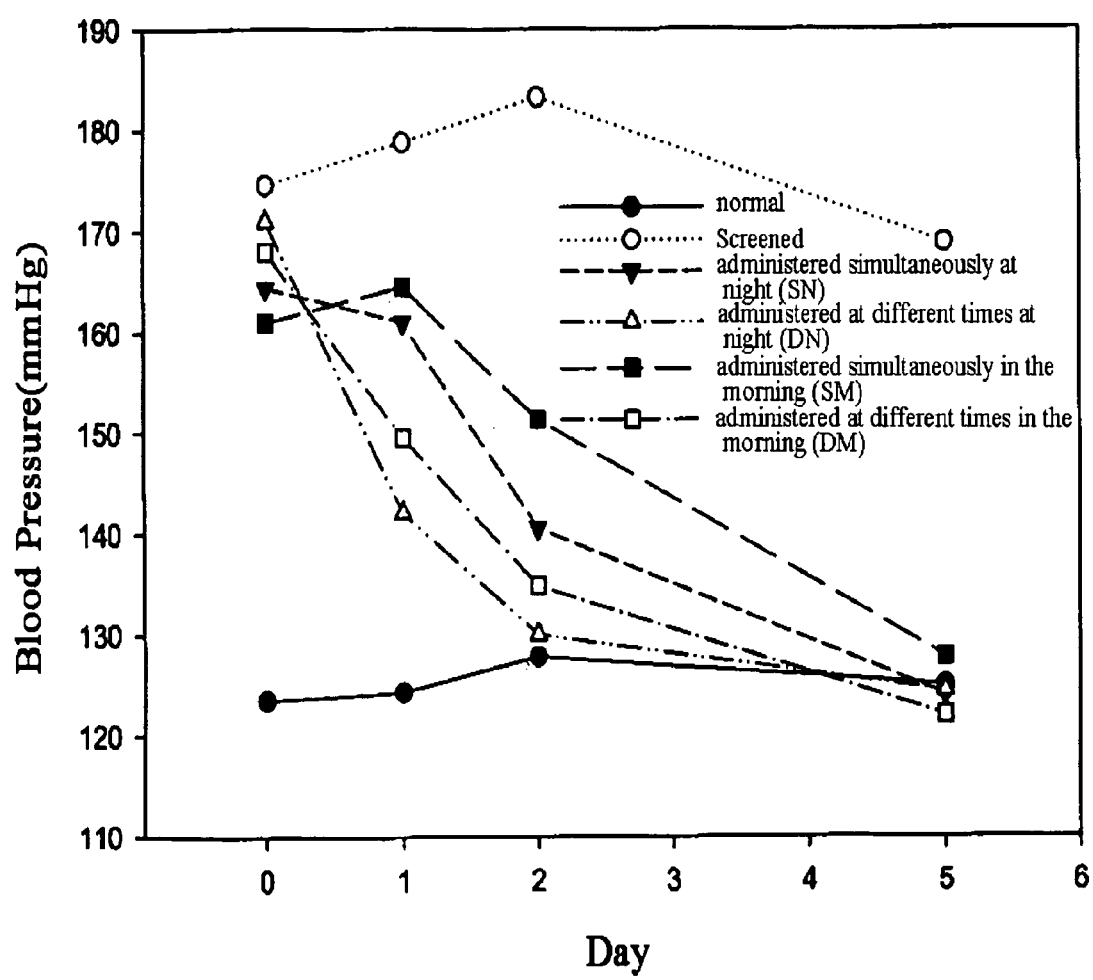
FIG. 8 is a graphic diagram shows the clinical study results of Test Example 8 and indicates the comparison of systolic blood pressure between dosage methods.
Figure 9:
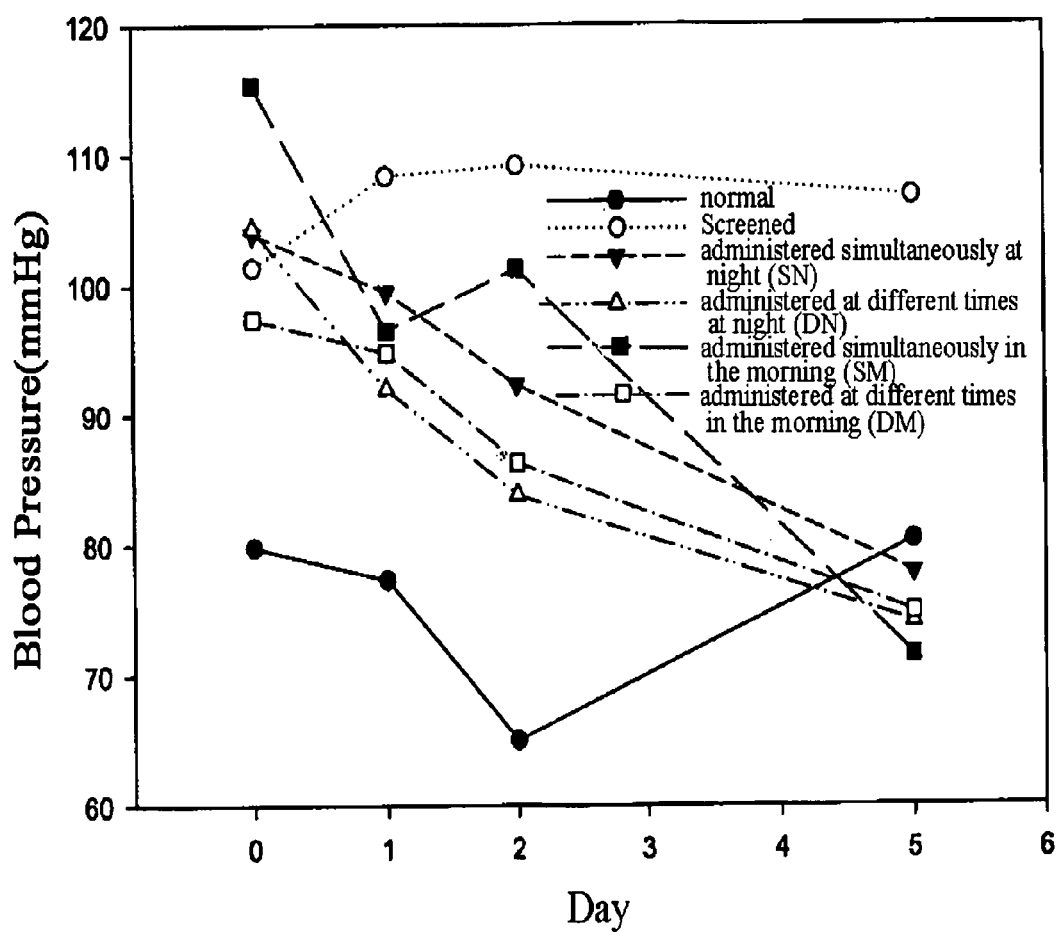
FIG. 9 is a graphic diagram shows the clinical study results of Test Example 8 and indicates the comparison of diastolic blood pressure between dosage methods.
Figure 10:
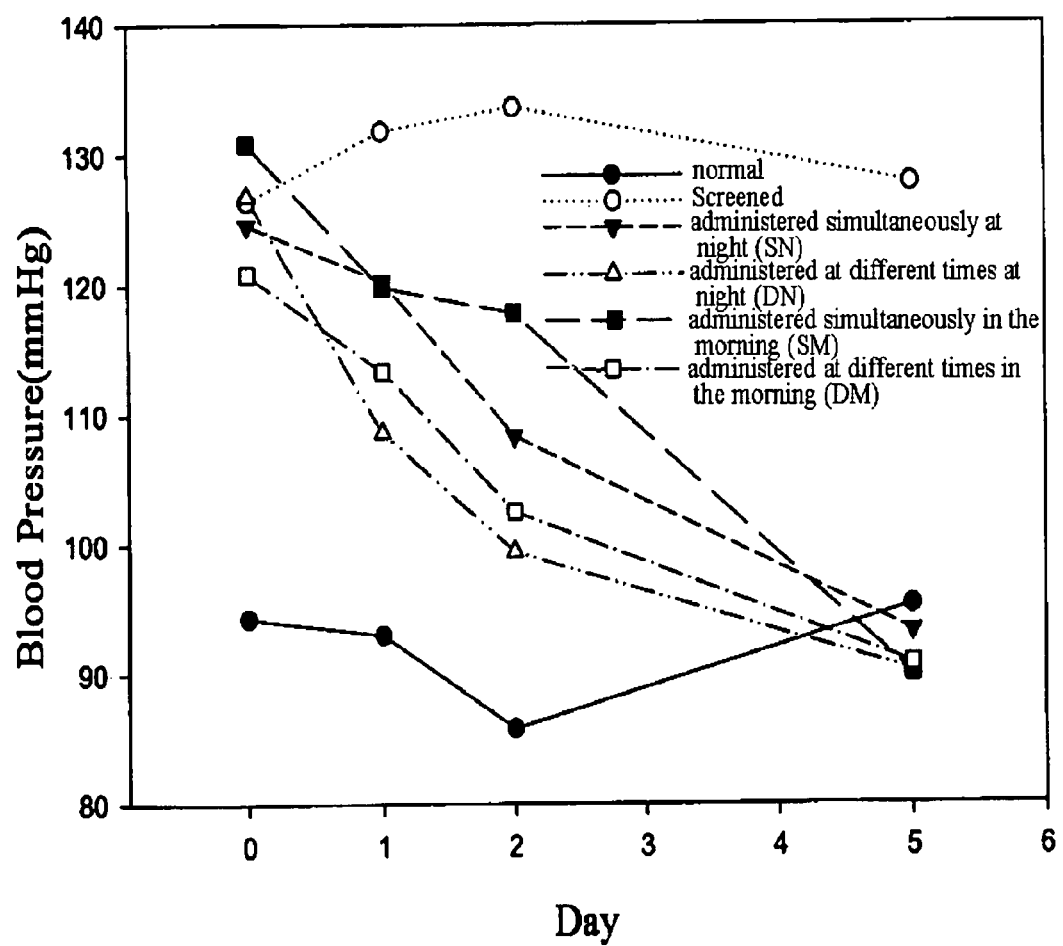
FIG. 10 is a graphic diagram shows the clinical study results of Test Example 8 and indicates the comparison of mean blood pressure between dosage methods.

Pharmacokinetics/pharmacodynamics in the results of the clinical animal study, performed in this Test Example, are shown in Table 8 below and FIGS. 8 to 10.

TABLE 8

Results of comparative animal study between administration at different times and simultaneous administration

| 1 | Items | WKY rats | SHR rats | SHR rats | SHR rats | SHR rats | SHR rats |
|---|---|---|---|---|---|---|---|
| 2 | Groups | Normal group | Triple-distilled water | Group administered simultaneously in the morning (dark conditions) | Group administered simultaneously in the evening (light conditions) | Group administered at different times in the morning (dark conditions) | Group administered at different times in the evening (light conditions) |
| 3 | Animal number | 4 | 5 | 5 | 5 | 5 | 5 |

State of animals at 20 hours after 5-day administration

| 4 | systolic blood pressure (mmHg) | 125.0 ± 5.5 | 168.8. ± 8.3 | 127.8 ± 10.5 | 124.0 ± 8.0 | 122.0 ± 9.5 | 124.4 ± 1.7 |
| 5 | diastolic blood pressure (mmHg) | 80.3 ± 15.5 | 106.8 ± 22.8 | 71.5 ± 17.3 | 77.8 ± 14.1 | 74.8 ± 11.0 | 74.0 ± 13.1 |
| 6 | Mean blood pressure (mmHg) | 95. ± 10.6 | 127.8 ± 13.9 | 90.0 ± 8.4 | 93.3 ± 8.4 | 90.8 ± 9.2 | 90.2 ± 9.8 |
| 7 | Pulse rate (rate/min) | 457.0 ± 55.0 | 439.0 ± 18.6 | 460.8 ± 74.3 | 498.8 ± 45.0 | 465.5 ± 30.4 | 463.6 ± 58.6 |

This animal study was performed on rats as test models under light conditions and dark conditions. The administration time applied in the animal study is conversely applied to humans, because the biorhythm of rats is opposite to the biorhythm of humans.

1. In blood pressure reducing effects, systolic blood pressure and diastolic blood pressure showed low values at day 5 compared to the screening group.

2. The blood pressure reducing effects are shown in FIGS. 8 to 10. It was observed that the group administered at different times in the evening (light conditions) was most excellent in the blood pressure reducing effect among the four groups.

Thus, it can be seen that, unlike the conventional group administered simultaneously, the composition of the present invention has the optimal blood pressure reducing effect during a time period from the morning to midday of the day following the administration thereof, when the average blood pressure reaches the climax.

It can be seen that, in the case of administration at different times, like the case of the novel combination product of this present invention comprising the angiotensin-II-receptor blocker and the HMG-CoA reductase inhibitor, the angiotensin-II-receptor blocker and the HMG-CoA reductase inhibitor, administered to reduce blood pressure, show an optimal antihypertensive effect compared to when single formulations of each of the angiotensin-II-receptor blocker and the HMG-CoA reductase inhibitor are simultaneously administered.

Meanwhile, Table 9 below shows the results of measurement of blood pressure and pulse rate in the group administered with losartan and simvastatin simultaneously and the inventive group administered at different times in the morning according to the present invention. As can be seen in Table 9, with respect to the blood pressure reducing effects of losartan and simvastatin, the test group administered at different times according to the present invention showed an increase of 0.3% in mean sitting systolic blood pressure compared to the group administered simultaneously, but the increase was not significant. Also, the inventive test group showed an increase of 4.8% in mean sitting diastolic blood pressure reducing effect, an increase of 3.3% in mean blood pressure reducing effect and an increase of 7.1% in pulse rate reducing effect, compared to the group administered simultaneously. Thus, the inventive test group showed a significant increase in the overall blood pressure-reducing effect.

TABLE 9

| Groups | Blood pressure (systolic) (mmHg) | Blood pressure (diastolic) (mmHg) | Blood pressure (mean) (mmHg) | Pulse rate (per min) |
| --- | --- | --- | --- | --- |
| Normal group | 125.0 ± 5.5 | 80.3 ± 15.5 | 95. ± 10.6 | 457.0 ± 55.0 |
| Screening group | 168.8 ± 8.3 | 106.8 ± 22.8 | 127.8 ± 13.9 | 439.0 ± 18.6 |
| Administered at different times in the evening | 124.4 ± 1.7 | 74.0 ± 13.1 | 90.2 ± 9.8 | 463.6 ± 58.6 |
| Administered simultaneously in the evening | 124.0 ± 8.0 | 77.8 ± 14.1 | 93.3 ± 8.4 | 498.8 ± 45.0 |
| Difference in blood pressure drop between simultaneous administration and administration at different times | −0.3% | +4.8% | +3.3% | +7.1% |

This animal study was performed on rats as test models under light/dark conditions. The administration time applied in the animal study is conversely applied to humans, because the biorhythm of rats is opposite to the biorhythm of humans.

Accordingly, through the delayed release of losartan administered after 4 hours as intended in the present invention in order to reduce blood pressure, it was demonstrated that the group administered with the drugs at different times had an excellent blood pressure-reducing effect compared to the group administered with the drugs simultaneously.

Test Example 9

Preliminary Clinical Test

For Example, in this clinical study was performed as described in Table 10 below in order to confirm the effect of the inventive combination. Specifically, in control groups, commercially available control "Zocor® tablet" (20 mg simvastatin; MSD) was administered alone, and "Zocor® tablet" and "Cozaar® tablet" (50 mg losartan potassium; MSD) were administered simultaneously. In a test group, "Zocor® tablet" and "Cozaar® tablet" were administered at different times, such that the release times of the drugs were the same as in the combination provided in Example of the present invention.

TABLE 10

| | | | |
| --- | --- | --- | --- |
| Title | Multi institutional clinical study was compare with the pharmacokinetic properties, effects and safety of administration with losartan and simvastatin simultaneously and administration with losartan and simvastatin at different times in hypertensive and hyperlipidemia patients (study research, investigator-initiated trial) | | |
| Object | To comparatively evaluate pharmacokinetic properties, effects and safety between a group administered with Zocor ® and Cozaar ® simultaneously and a group administered with the drugs at different times after administration once a day for 6 weeks (42 days) in hypertension and hyperlipidemia patients. | | |
| Subjects | Seventeen 30-60-year-old patients having hypertension and hyperlipidemia; 8 patients administered with the drugs simultaneously and 9 patients administered with the drugs at different times. | | |
| Design | This test was designed as follows:<br>2-open labeled, and single dose.<br>Test drug 1: 50 mg Cozaar ® (one tablet)<br>Test drug 2: 20 mg Zocor ® (one tablet).<br>Group A: administered with with Zocor ® and Cozaar ® simultaneously in the evening.<br>Group B: administered with with Zocor ® and Cozaar ® at different times in the evening.<br>The drugs were administered for 6 weeks (42 days), and the comparison between the two groups was performed. | | |
| Efficacy and Safety | 1. Efficacy evaluation<br>Primary endpoint: comparison of changes (between before treatment and end of study) in mean systolic blood pressure and LDL-C, between two groups, i.e., the group administered simultaneously and the group administered at different times.<br>Second endpoints: comparison of changes (between before treatment and end of study) in mean sitting diastolic pressures and pulse pressure, lipid profiles (total cholesterol (mg/dl), LDL-cholesterol (mg/dl), HDL-cholesterol (mg/dl), triglyceride (mg/dl), other risk factors (Apo B, HDL-C/LDL-C)), and CV risk group, between the two groups.<br>2. Safety evaluation<br>Physical examination, vital sign, adverse events, ECG etc. | | |
| | | Administered drugs and | |
| | Group name | method | Number of patients |
| Test groups | Group administered at different times in the evening | Administered with 20 mg Zocor ® at 7 p.m., and after 4 hours, administered with 50 mg Cozaar ® at 11 p.m. | 9 |

TABLE 10-continued

|  |  |  |
|---|---|---|
| Group administered simultaneously in the evening | Administered with 50 mg Cozaar ® and 20 mg Zocor ® simultaneously at 7 p.m. | 8 |

This study supports the effects of the present invention and used marketed drugs and was performed in small patient group according to ICH-GCP and KGCP. Lipids measured at 42 days (fasted) after the start of administration in this clinical study are shown in Table 11 below.

TABLE 11

| Lipids | Group A (administered simultaneously; 8 patients) | | | Group B (administered at different times; 9 patients) | | | Results |
|---|---|---|---|---|---|---|---|
|  | Screening | D42 | Change (%) | Screening | D42 | Change (%) |  |
| Total cholesterol (120-230 mg/dl) | 208.6 | 151.3 | −57.4 (27.5%) | 251.1 | 172.3 | −78.8 (31.4%) | Group B was better. |
| LDL-cholesterol (0-120 mg/dl) | 139.6 | 82.6 | −57.00 (40.8%) | 174.2 | 95.1 | −79.1 (45.4%) | Group B was better. |
| HDL/LDL | 0.302 | 0.519 | 0.217 (71.9%) | 0.312 | 0.538 | 0.226 (72.4%) | The two groups showed a significant increase |
| Triglyceride (40-150) | 177.5 | 175.9 | −1.6 (0.9%) | 172.4 | 161.4 | −11.0 (6.4%) | Group B was better. |

Blood pressure, pulse rate and pulse pressure, measured at 41 days after the start of administration in this clinical test, are shown in Table 12 below.

TABLE 12

| | Group A (administered simultaneously; 8 patients) | | | Group B (administered at different times; 9 patients) | | | Results |
|---|---|---|---|---|---|---|---|
|  | Screening | D41 | Change | Screening | D41 | Change |  |
| BP (SYS) | 148.3 | 141.3 | −7.0 (4.7%) | 145.2 | 132.4 | −12.7 (8.7%) | Group B was better |
| BP (DYS) | 99.4 | 90.0 | −9.4 (9.5%) | 94.8 | 80.9 | −13.9 (14.7) | Group B was better |
| Pulse pressure | 53.1 | 51.3 | −1.8 (3.4%) | 50.8 | 51.5 | 0.7 (3.3%) | Similar |
| Pulse rate | 76.5 | 83.8 | 7.3 (9.5%) | 72.3 | 76.3 | 4.0 (5.5%) | Group B was better |

Biomarkers measured at 41 days after the start of administration in this clinical test are shown in Table 13 below.

TABLE 13

| | Group A (administered simultaneously; 8 patients) | | | Group B (administered at different times; 9 patients) | | | Results |
|---|---|---|---|---|---|---|---|
|  | Screening | D42 | Change | Screening | D42 | Change |  |
| AST (0-50 IU/L) | 25.4 | 27.4 | 2.0 (7.9%) | 26.1 | 28.0 | 1.9 (7.3%) | Similar |
| ALT (0-45 IU/L) | 40.4 | 41.4 | 1.0 (2.5%) | 37.1 | 34.7 | −2.44 (6.6%) | Group B was better |

TABLE 13-continued

| | Group A (administered simultaneously; 8 patients) | | | Group B (administered at different times; 9 patients) | | | Results |
|---|---|---|---|---|---|---|---|
| | Screening | D42 | Change | Screening | D42 | Change | |
| r-GTP (4-50) | 63.1 | 68.0 | +4.9 (7.8%) | 38.2 | 38.7 | +0.5 (1.3%) | Group B was better |
| CPK (51-246 IU/L) | 157.8 | 117.5 | −40.3 (25.5%) | 82.9 | 84.8 | 1.9 (2.3%) | Maintained in the normal range (A > B). |

From the clinical study results for the group administered with simvastatin and losartan at different times and the group administered with the drugs simultaneously, it was proven that the group administered with simvastatin and losartan at different times was excellent in all evaluation parameters including blood pressure reducing, lipid reduction and side effect-associated biomarkers. Especially, in test group was no serious adverse events other than non-serious event, which generally occur upon the administration of each of simvastatin and losartan.

As a result, it was demonstrated through said clinical test that, when the angiotensin-II-receptor blocker and the HMG-CoA reductase inhibitor are administered at different times according to the present invention, the HMG-CoA reductase inhibitor shows a more excellent antihyperlipemial effect even at the same dose, compared to when single formulations of each of the angiotensin-II-receptor blocker and the HMG-CoA reductase inhibitor are administered simultaneously. In addition, the enhanced blood pressure-reducing effect of the angiotensin-II-receptor blocker administered in order to reduce blood pressure was demonstrated, and it can be seen that the angiotensin-II-receptor blocker shows the optimal effect due to the extension of the release time thereof.

INDUSTRIAL APPLICABILITY

As described above, the present invention relates to a lag time delayed-release formulation comprising of an angiotensin-II-receptor blocker and an HMG-CoA reductase inhibitor and provides a pharmaceutical combination comprising an angiotensin-II-receptor blocker and an HMG-CoA reductase inhibitor, which is most suitable for the prevention and treatment of hypertension having or not having Complication such as cardiovascular, cardiopulmonary, pulmonary or renal disorders, metabolic syndromes including insulin resistance and, diabetes or prediabetes.

Specifically, the present invention provides a drug delivery system, which comprises a lag time delayed-release material and an immediate release material, such that the dissolution time of each of the angiotensin-II-receptor blocker in body and the HMG-CoA reductase inhibitor can be controlled, and thus each of the drugs can be released at a specific rate in the body. The drug delivery system is a lag time delayed-release formulation, which is designed with the consideration of the absorption, the metabolism and the pharmacological action of each drugs, so as to obtain the most ideal efficacy and safety when it is administered once a day in the evening.

Also, the present invention provides a preparation method of the lag time delayed-release combination.

The invention claimed is:

1. A lag-time delayed release combination pharmaceutical composition for oral administration comprising
   (a) a delayed-release portion comprising a therapeutically effective amount of a release-controlling material and an angiotensin-II-receptor blocker selected from the group consisting of losartan, valsartan, irbesartan, candesartan, telmisartan, eprosartan, olmesartan, and pharmaceutically acceptable salts thereof; and
   (b) an immediate release portion comprising a therapeutically effective amount of an HMG-CoA reductase inhibitor selected from the group consisting of simvastatin, lovastatin, atorvastatin, pitavastatin, rosuvastatin, fluvastatin, pravastatin, pharmaceutically acceptable salts thereof and mixtures thereof,
wherein more than 80% of the HMG-CoA reductase inhibitor is released within one hour, and less than 10% of the angiotensin-II-receptor blocker is released after up to two hours, when tested with a paddle dissolution method at 50 rpm in artificial gastric juice for two hours and artificial intestinal juice thereafter.

2. The pharmaceutical composition according to claim 1, wherein said pharmaceutical composition releases less than 40 wt % of the angiotensin-II-receptor blocker up to 4 hours after oral administration, such that the angiotensin-II-receptor blocker is absorbed in the liver 3-4 hours later than the HMG-CoA reductase inhibitor.

3. The pharmaceutical composition according to claim 2, wherein said pharmaceutical composition releases less than 30 wt % of the amount of the angiotensin-II-receptor blocker up to 4 hours after oral administration.

4. The pharmaceutical composition according to claim 1, wherein said pharmaceutical composition releases the angiotensin-II-receptor blocker 4 hours after administration.

5. The pharmaceutical composition according to claim 1, wherein the angiotensin-II-receptor blocker is losartan.

6. The pharmaceutical composition according to claim 1, wherein the angiotensin-II-receptor blocker is losartan potassium.

7. The pharmaceutical composition according to claim 1, wherein the delayed-release portion comprises 5-1200 mg of the angiotensin-II-receptor blocker.

8. The pharmaceutical composition according to claim 1, wherein the HMG-CoA reductase inhibitor is at least one selected from the group consisting of simvastatin, lovastatin, and atorvastatin.

9. The pharmaceutical composition according to claim 8, wherein the HMG-CoA reductase inhibitor is simvastatin.

10. The pharmaceutical composition according to claim 1, wherein the immediate release portion comprises 5-160 mg of the HMG-CoA reductase inhibitor.

11. The pharmaceutical composition according to claim 1, wherein the release-controlling material is at least one selected from the group consisting of an enteric polymer, a water-insoluble polymer, a hydrophobic compound and a hydrophilic polymer.

12. The pharmaceutical composition according to claim 11, wherein the release-controlling material is present in an amount of 10-500 parts by weight based on 100 parts by weight of the angiotensin-II-receptor blocker.

13. The pharmaceutical composition according to claim 11, wherein the enteric polymer is at least one selected from the group consisting of polyvinyl acetate phthalate, methacrylic acid copolymers, hydroxypropylmethylcellulose phthalate, shellac, cellulose acetate phthalate, cellulose propionate phthalate, Eudragit L and Eudragit S.

14. The pharmaceutical composition according to claim 11, wherein the water-insoluble polymer is at least one selected from the group consisting of polyvinyl acetate, poly(ethylacrylate, methylmethacrylate) copolymers and poly(ethylacrylate, methyl methacrylate, trimethylaminoethylmethacrylate) copolymers, ethyl cellulose and cellulose acetate.

15. The pharmaceutical composition according to claim 11, wherein the hydrophobic compound is at least one selected from the group consisting of fatty acid, fatty acid ester, fatty acid alcohol, wax and inorganic material.

16. The pharmaceutical composition according to claim 15, wherein the fatty acid or fatty acid ester is glyceryl palmitostearate, glyceryl stearate, glyceryl behenate, cetyl palmitate, glyceryl monooleate or stearic acid; the fatty acid alcohol is cetostearyl alcohol, cetyl alcohol or stearyl alcohol; the wax is Carnauba wax, beewax or microcrystalline wax; the inorganic material is talc, precipitated calcium carbonate, dibasic calcium phosphate, zinc oxide, titanium oxide, kaolin, bentonite, montmorillonite or veegum.

17. The pharmaceutical composition according to claim 11, wherein the hydrophilic polymer is at least one selected from the group consisting of saccharides, cellulose derivatives, gums, proteins, polyvinyl derivatives, polymethacrylate copolymers, polyethylene derivatives and carboxyvinyl polymers.

18. The pharmaceutical composition according to claim 16, wherein the hydrophilic polymer is at least one selected from the group consisting of dextrin, polydextrin, dextran, pectin and pectin derivatives, alginate, polygalacturonic acid, xylan, arabinoxylan, arabinogalactan, starch, hydroxypropyl starch, amylase, amylopectin; hydroxypropylmethyl cellulose, hydroxypropyl cellulose, hydroxymethyl cellulase, hydroxyethyl cellulose, methyl cellulose, carboxymethyl cellulose sodium, hydroxypropyl methylcellulose acetate succinate, hydroxyethylmethylcellulose, guar gum, locust bean gum, tragacanth, carrageenan, gum acacia, gum arabic, gellan gum, xanthan gum gelatin, casein, zein polyvinyl alcohol, polyvinyl pyrrolidone, polyvinylacetal diethylaminoacetate poly(butyl methacrylate, (2-dimethylaminoethyl)methacrylate, methylmethacrylate) copolymers, poly(methacrylic acid, methylmethacrylate) copolymers and poly(methacrylic acid, ethylacrylate) copolymers, polyethylene glycol, polyethylene oxide and carbomer.

19. The pharmaceutical composition according to claim 1, wherein said composition is in the form of a single tablet existing as a two-phase matrix in which the delayed-release portion exists as a discontinuous phase, such that the angiotensin-II-receptor blacker is released slowly, and the immediate release portion exists as a continuous phase, such that the HMG-CoA reductase inhibitor is released immediately.

20. The pharmaceutical composition according to claim 1, wherein the delayed-release portion and the immediate release portion constitute a multilayered structure.

21. The pharmaceutical composition according to claim 1, wherein said composition is in the form of a single tablet having a dual layer structure which consists of an inner core comprising the delayed-release portion and an outer layer comprising the immediate release portion and covering the outer surface of the inner core.

22. The pharmaceutical composition according to claim 1, wherein said composition is in the form of a capsule comprising granules consisting of the delayed-release portion and granules consisting of the immediate release portion.

23. The pharmaceutical composition according to claim 1, wherein said composition is in the form of a tablet.

24. The pharmaceutical composition according to claim 23, wherein said tablet comprises a coating layer.

25. The pharmaceutical composition according to claim 24, wherein the coating layer comprises at least one selected from the group consisting of cellulose derivatives, sugar derivatives, polyvinyl derivatives, waxes, fats, gelatin, polyethylene glycol, ethyl cellulose, titanium oxide and diethyl phthalate.

26. The pharmaceutical composition according to claim 24, wherein the coating layer comprised in an amount of 0.5-15 wt % based on the total weight of the tablet.

27. The pharmaceutical composition of claim 1 wherein the composition is administered once a day between 5 p.m. and 10 p.m., as antihypertensive and antihyperlipidemic agent.

28. The pharmaceutical composition according to claim 1, wherein said pharmaceutical composition releases less than 20% of the angiotensin-II-receptor blocker 4 hours after administration.

29. The pharmaceutical composition according to claim 1, wherein said pharmaceutical composition begins releasing the angiotensin-II-receptor blocker 4 hours after the HMG-CoA reductase inhibitor begins releasing.

30. A method for treating a cardiovascular, cardiopulmonary, pulmonary or renal disease, comprising administering to a patient in need of such treatment a therapeutically effective amount of a composition of claim 1.

31. The method of claim 30, wherein the cardiovascular disease is at least one selected from hypertension, coronary heart diseases and hyperlipidemia.

32. The method of claim 31, wherein the cardiovascular disease is accompanied by at least one complication selected from metabolic syndrome, insulin resistance, diabetes or prediabetes.

33. The method of claim 30, wherein said pharmaceutical composition releases less than 30% of the angiotensin-II-receptor blocker 4 hours after administration.

34. The method of claim 30, wherein said pharmaceutical composition releases less than 20% of the angiotensin-II-receptor blocker 4 hours after administration.

35. The method of claim 30, wherein said pharmaceutical composition releases the angiotensin-II-receptor blocker 4 hours after administration.

36. The method of claim 30, wherein said pharmaceutical composition is administered once a day between 5 p.m. and 10 p.m.

37. The method of claim 30, wherein the composition is administered once a day at 7 p.m.

38. A method for treating a patient suffering from combined hypertension and hyperlipidemia comprising administering to said patient a therapeutically effective amount of the composition of claim 1.

39. The method of claim 38, wherein the hypertension is non-dipper hypertension.

40. The pharmaceutical composition of claim 1, wherein after administration, at least 90% of said 3-hydroxy-3-methylglutaryl-coenzyme A reductase inhibitor is released before 30% of said angiotensin-II-receptor blocker is released.

41. The pharmaceutical composition of claim 1, wherein at least 90% of said 3-hydroxy-3-methylglutaryl-coenzyme A reductase inhibitor is released within one hour after administration.

42. The pharmaceutical composition according to claim 1, whereby the efficacy of the HMG-CoA reductase inhibitor and angiotensin-II-receptor blocker is increased and the antagonism between the angiotensin-II-receptor and the HMG-CoA reductase inhibitor is decreased so as to reduce side effects.

* * * * *

UNITED STATES PATENT AND TRADEMARK OFFICE
CERTIFICATE OF CORRECTION

PATENT NO. : 8,642,083 B2  Page 1 of 1
APPLICATION NO. : 12/513054
DATED : February 4, 2014
INVENTOR(S) : Kim et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 212 days.

Signed and Sealed this

Twenty-second Day of September, 2015

Michelle K. Lee
*Director of the United States Patent and Trademark Office*